(12) United States Patent
Plückthun et al.

(10) Patent No.: US 7,858,088 B2
(45) Date of Patent: *Dec. 28, 2010

(54) METHOD FOR THE STABILIZATION OF CHIMERIC IMMUNOGLOBULINS OR IMMUNOGLOBULIN FRAGMENTS, AND STABILIZED ANTI-EGP-2 SCFV FRAGMENT

(75) Inventors: Andreas Plückthun, Zürich (CH); Annemarie Honegger, Zürich (CH); Jörg Willuda, Berlin (DE)

(73) Assignee: University of Zurich, Zurich (CH)

( * ) Notice: Subject to any disclaimer, the term of this patent is extended or adjusted under 35 U.S.C. 154(b) by 38 days.

This patent is subject to a terminal disclaimer.

(21) Appl. No.: 11/969,059

(22) Filed: Jan. 3, 2008

(65) Prior Publication Data

US 2008/0299124 A1 Dec. 4, 2008

Related U.S. Application Data

(62) Division of application No. 11/024,877, filed on Dec. 30, 2004, now Pat. No. 7,341,722, which is a division of application No. 09/971,543, filed as application No. PCT/EP00/03176 on Apr. 10, 2000, now Pat. No. 7,033,798.

(30) Foreign Application Priority Data

Apr. 9, 1999 (EP) .............................. 99 10 7030

(51) Int. Cl.
*A61K 39/395* (2006.01)
*A61P 31/00* (2006.01)
*C07K 16/18* (2006.01)

(52) U.S. Cl. ............... 424/133.1; 424/178.1; 430/391.7

(58) Field of Classification Search .............. 424/133.1, 424/178.1; 530/391.7
See application file for complete search history.

(56) References Cited

U.S. PATENT DOCUMENTS 7,341,722 B2 * 3/2008 Pluckthun et al. ......... 424/133.1
2005/0136049 A1 6/2005 Ledbetter et al.

FOREIGN PATENT DOCUMENTS

WO 2004096271 11/2004

OTHER PUBLICATIONS

Gibson et al., Proteins 3:155-60, 1988.
Knappik et al., Protein Engineering 8:81-89, 1995.
Saul et al ., J Mol. Biol 230:15-20, 1993.
Al-Lazikani et al., "Standard Conformations for the Canonical Structures of Immunoglobulins", J. Mol. Biol., 1997, p. 927-948, vol. 273, Academic Press Limited.
Bothmann et al., "Selection for a periplasmic factor improving Phage display and functional periplasmic expression", Nature Biotechnology, Apr. 1998, pp. 376-380, vol. 16.
Carter et al., "Engineering antibodies for imaging and therapy", Protein Engineering, pp. 449-454, vol. 8 Current Op. Biotech (1997).
Carter et al., "Humanization of an anti-p185.sup.HER2 antibody for human cancer therpay", Proc. Natl. Acad. Sci. USA, May 1992, pp. 4285-4289, vol. 89, Immunology.
Eigenbrot et al., "X-ray Structures of the Antigen binding Domains from Three Variants of Humanized anti-185.sup. HER2 Antibody 4D5 and Comparison with Molecular Modeling", J. Mol. Biol. 1993, pp. 969-995, vol. 229, Academic Press Limited.
Glockshuber et al., "A Comparison of Strategies to Stabilize Immunoglobulin F.sub.v-Fragments", Biochemistry, 1990, pp. 1362-1367, vol. 29, No. 6, American Chemical Society.
Helfrich et al., "Construction and Characterization of a Bispecific Diabody for Retargeting T Cells to Human Carcinomas", Int. J. Cancer, 1998, pp. 232-239, vol. 26, Wiley-Liss, Inc.
Jung et al, "Improving in vivo folding and stability of a single-chain Fv antibody fragment by loop grafting", Protein Engineering, 1997, pp. 959-966, vol. 10, No. 8, Oxford University Press.
Knappik et al., "Engineered turns of a recombinant antibody improve its in vivo folding", Protein Engineering, Jan. 1995, pp. 81-89, No. 1.
Langedijk et al., "The Nature of Antibody Heavy Chain Residue H6 Strongly Influences of a V.sub.H Domain Lacking the Disulfide Bridge", J. Mol. Biol., 1998, pp. 95-110, vol. 283, Academic Press.
Pluckthun et al., "New protein engineering approaches to multivalent and bispecific antibody fragments", Immunotechnology, 1997, pp. 83-105, vol. 3, Elsevier.
Proba et al., "Antibody scFv Fragments Without Disulfide Bonds Made by Molecular Evolution", J. Mol. Biol., 1998, pp. 245-253, vol. 275, Academic Press Limited.
Saul et al., "Structural Patterns at Residue Positions 9, 18, 67 and 82 in the V.sub.H Framework Regions of Human and Murine Immunoglobulins", J. Mol. Biol., 1993, pp. 15-20, vol. 230, Academic Press Limited.
Worn et al., "An intrinsically stable antibody scFv fragment can tolerate the loss of both disulfide bonds and fold correctly", FEBS Letters, 1998, pp. 357-361, vol. 427, Federation of European Biochemical Societies.
Stratagen Catalog (1998) (pp. 1-2).
Dermer Biotechnology 12: 320, 1994.
Gura et al (Science vol. 278 Nov. 1997 1041-1042).
Seaver (1994; Genetic Engineering vol. 14(14):pp. 10 and 21.
Willuda J., et al. "Rational engineering for high stability is required for tumor targeting of a high-affinity scFv fragment specific for the panepithelial glycoprotein egp-2." Proceedings of the American Association for Cancer Research Annual Meeting (Mar. 1999), vol. 40, O. 354, Abst. 2343, Meeting Info,: 90th Annual Meeting of the American Association for Cancer Research, Philadelphia, PA, USA, Apr. 10-14, 1999.

(Continued)

Primary Examiner—Lynn Bristol
(74) Attorney, Agent, or Firm—Dann, Dorfman, Herrell & Skill; Kathleen D. Rigaut

(57) ABSTRACT

The present invention relates to a method for stabilizing chimeric immunoglobulins or immunoglobulin fragments. Furthermore, the invention also provides a stabilized anti-EGP-2 scFv fragment.

7 Claims, 7 Drawing Sheets

OTHER PUBLICATIONS

Krebber, A., et al. "Reliable cloning of functional antibody variable domains from hybridomas and spleen cell repertoires employing a reengineered phage display system." J. Immunol. Meth., 201(1): 35-55 (Feb. 14, 1997).

Jung, S., et al. "Improving in vico folding and stability of a single-chain Fv antibody fragment by loop grafting." Protein Engineering, 10(8): 959-66 (Aug. 1997).

Proba, K., et al. "Antibody scFv fragments without disulfide bonds made by molecular evolution." J. Molec. Biol., 275 (2): 245-53 (Jan. 16, 1998).

Willuda J., et al. "High thermal stability is essential for tumor targeting of antibody fragments: Engineering of a humanized anti-epithelial glycoprotein-2 (Epithelial cell adhesion molecule) single-chain Fv fragment." Cancer Research, 59(22): 5758-5767 (Nov. 15, 1999).

Waibel, R., et al. "Stable one-step technetium -99m labeling of His-tagged recombinant proteins with a novel Tc(I)- carbonyl complex." Nature Biotechnology 17(9): 897-901 (Sep. 1999).

* cited by examiner

Figure 1A

METHOD FOR THE STABILIZATION OF CHIMERIC IMMUNOGLOBULINS OR IMMUNOGLOBULIN FRAGMENTS, AND STABILIZED ANTI-EGP-2 SCFV FRAGMENT

This application is a Divisional application of U.S. patent application Ser. No. 11/024,877 filed Dec. 30, 2004 (now U.S. Pat. No. 7,341,722), which is a divisional of U.S. patent application Ser. No. 09/971,543, now U.S. Pat. No. 7,033,798, which is §371 Application of PCT/EP00/03176 filed Apr. 10, 2000, the contents of each of the foregoing applications are incorporated by reference herein.

FIELD OF THE INVENTION

The present invention relates to a method for stabilizing chimeric immunoglobulins or immunoglobulin fragments. Furthermore, the invention also provides a stabilized anti-EGP-2 scFv fragment.

BACKGROUND OF THE INVENTION

Small antibody fragments show exciting promise for use as therapeutic agents, diagnostic reagents, and for biochemical research. Thus, they are needed in large amounts, and the expression of antibody fragments, e.g. Fv, single-chain Fv (scFv), or Fab in the periplasm of *E. coli* (Skerra & Plückthun 1988; Better et al., 1988) is now used routinely in many laboratories. Expression yields vary widely, however, especially in the case of scFvs. While some fragments yield up to several mg of functional, soluble protein per litre and OD of culture broth in shake flask culture (Carter et al., 1992, Plückthun et al. 1996), other fragments may almost exclusively lead to insoluble material, often found in so-called inclusion bodies. Functional protein may be obtained from the latter in modest yields by a laborious and time-consuming refolding process. The factors influencing antibody expression levels are still only poorly understood. Folding efficiency and stability of the antibody fragments, protease ability and toxicity of the expressed proteins to the host cells often severely limit actual production levels, and several attempts have been tried to increase expression yields. For example, Knappik & Plückthun (1995) have identified key residues in the antibody framework which influence expression yields dramatically. Similarly, Ullrich et al. (1995) found that point mutations in the CDRs can increase the yields in periplasmic antibody fragment expression. Nevertheless, these strategies are only applicable to a few antibodies.

The observations by Knappik & Plückthun (1995) indicate that optimising those parts of the antibody fragment which are not directly involved in antigen recognition can significantly improve folding properties and production yields of recombinant Fv and scFv constructs. The causes for the improved expression behaviour lie in the decreased aggregation behaviour of these molecules. For other molecules, fragment stability and protease resistance may also be affected. The understanding of how specific sequence modifications change these properties is still very limited and currently under active investigation.

Single-chain Fv fragments (scFvs) are recombinant antibody fragments consisting of the variable domains of the heavy and light chain, connected by a flexible peptide linker[12, 13]. These fragments conserve the monovalent binding affinity and the specificity of the parent mAb and can be efficiently produced in bacteria[14]. ScFvs can be constructed by cloning the variable domains of a mAb showing interesting binding properties from hybridoma cells or by direct selection of scFv fragments with the desired specificity from immunized or naive phage libraries[15,16]. Frequently scFvs cloned from hybridomas show poor production yields and low thermodynamic stability which limit their usefulness for in vivo applications[17], whereas scFvs selected from phage libraries have already undergone selection not only for antigen binding, but also for stability and folding properties in the scFv format[18].

For therapeutic applications, human antibodies or antibody fragments are preferred to avoid an immune response e.g. against a murine antibody fragment derived from a monoclonal antibody (HAMA response). To solve that problem, human antibody fragments can be obtained by screening human antibody libraries (EP-A1 0 859 841; Vaughan et al., 1996). Another solution is to transplant the specificity of a non-human monoclonal antibody by grafting the CDR regions onto a human framework (EP-B1 0 239 400). In an improvement of said technique, humanized antibodies or antibody fragments with improved binding behavior can be produced by incorporating additional residues derived from said non-human antibody (EP-B1 0 451 216). In addition to achieving humanization, these techniques allow to "repair" scFv fragments with suboptimal stability and/or folding yield by grafting of the CDRs of a scFv fragment with the desired binding affinity and specificity onto the framework of a different, better behaved scFv, as was shown for the fluorescein binding antibody fragment 4-4-20 whose CDRs were grafted on the 4D5-framework, leading to a clear improvement of both expression yield and thermodynamic stability[18] The 4D5 framework itself is an artificial framework resulting from the human consensus sequence and was used for the humanization of the anti-c-erbB2 (p185$^{Her2}$-ECD) 4D5 mAb (Herceptin™)[19]. Later studies showed the above average thermodynamic stability of the 4D5 antibody fragment[20], which correlates to the thermal stability of this molecule (Wörn and Plückthun, 1999) and is apparently of general importance for the in vivo application of scFvs.

The murine monoclonal antibody (mAb) MOC31 recognizes the 38 kDa transmembrane epithelial glycoprotein-2[1] (EGP-2; also known as GA733-2, Ep-CAM or KSA). EGP-2 is regarded as a suitable target antigen for tumor imaging and therapy, since it is highly overexpressed on a variety of human carcinomas and is not shed into the circulation. Several clinical trials with anti-EGP-2 mAbs such as 17-1A, KS1/4 and MOC31[2,3,4] demonstrated the potential of these antibodies for active and passive immunotherapy of human carcinomas. The exact function of the transmembrane glycoprotein EGP-2 is not yet known, although a role in cell-cell association has been proposed (Simon et al., 1990). Recent reports identify EGP-2 as a homophilic cell-cell adhesion molecule[5,6], and EGP-2 has been identified as a potential modifier of invasiveness and chemoresponsiveness[7]. In a study evaluating the potential of new immunotherapeutics targeted to EGP-2, exotoxin-A (ETA) chemically fused to mAb MOC31 was found to retard the growth of large tumors[8].

Carcinoma-associated antigens such as c-erbB2 and EGF-receptor, as well as EGP-2 have served as targets for radiolabelled antibodies for tumor imaging and therapy. Effort have been made to improve the targeting efficiency by reducing the molecular weight and thereby increasing the tissue penetration and serum clearance of such antibody-based constructs. Fab, (Fab)$^2$, dsFv and scFv fragments, generated by recombinant antibody technology, have great potential in this respect[9,10], although up to now the optimal formats concerning stability, molecular weight and affinity have not been determined and have to be fine-tuned for the different antibody-effector fusion proteins depending on the special in vivo system and application goal[11].

For the development of new antibody fragment based imaging and therapeutic reagents directed to the pancarcinoma associated antigen epithelial glycoprotein-2 the variable domains of the murine anti-EGP-2 hybridoma MOC31 was cloned in the single-chain Fv fragment format[16]. Although the resulting scFv showed the expected binding affinity and specificity towards EGP-2, which was also shown on tissues sections in immunohistostaining experiments by others[30], it was poorly expressed in the periplasm of bacteria. In vivo targeting experiments in nude mice employing this scFv fragment failed. The scFv not only did not accumulate in the tumor, but also showed slower clearance rates than an irrelevant control scFv directed against fluorescein. It could be shown that the MOC31 scFv formed high molecular weight aggregates and rapidly lost its activity when incubated in serum at body temperature (37° C.). This was primarily due to insufficient thermal stability rather than proteolytic degradation, since similar precipitation and loss of immunoactivity could also be observed upon incubation of highly purified scFv in PBS at 37° C.

To derive from this aggregation-prone and thermally unstable scFv a molecule suitable for immunotherapeutic application, the biophysical properties of the construct had to be improved. Basically, two avenues were open to approach this goal: In-vitro evolution of the MOC31 scFv towards better thermal stability by combining randomization with selection for improved functionality[35] at elevated temperature or the transfer of the binding specificity of the anti-EGP-2 scFv MOC31 onto a scFv framework with above average biophysical properties by CDR grafting[18]. Although the first option has been successfully used to achieve extremely stable scFvs[35], the second option had the added advantage that by choosing a human framework sequence for the graft, a humanization could be achieved at the same time, thus reducing the potential immunogenicity of future immunotherapeutic reagents. It was therefore decided to graft the anti-EGP-2 scFv MOC31 binding specificity onto the artificial human consensus framework of scFv 4D5, essentially corresponding to the germline sequences IGVH 3-66 and IGVK 1-39 (IMGT). Grafting of complementary determining regions (CDRs) of mAbs for humanization has been used more than 100 times for humanization[10] and can now be regarded as a standard technology. The 4D5 framework has been used successfully several times before as an CDR acceptor[21,18,36].

This strategy proved successful, since the graft variant 4D5MOC-A showed binding characteristics indistinguishable to those of the parent antibody and scFv.

However, 4D5MOC-A showed only a thermal stability intermediate between that of the two parent molecules 4D5 and MOC31.

Biodistribution data indicated, that scFv MOC31, which lost most of its activity within less than 1 hour at 37° C. failed to enrich at the tumor, the graft variant 4D5MOC-A, stable for a few hours at 37° C. enriched only slightly.

DESCRIPTION OF THE INVENTION

Thus, the technical problem underlying the present invention is to provide a method which enables the stabilization of chimeric immunoglobulins or immunoglobulin fragments formed by CDR-grafting approaches. A further technical problem underlying the present invention is to stabilize the chimeric anti-EGP-2-binding scFv fragment 4D5MOC-A. The solution to the above technical problems is achieved by the embodiments characterized in the claims. Accordingly, the present invention allows to identify and modify residues of the chimeric immunoglobulins or immunoglobulin fragments which lead to increased stability. The technical approach of the present invention, i.e. the identification and exchange of amino acid residues in the framework regions of the VH domain to stabilize chimeric immunoglobulins or immunoglobulin fragments formed by CDR-grafting approaches is neither provided nor suggested by the prior art.

Thus, the present invention relates to a method for stabilizing a chimeric immunoglobulin or immunoglobulin fragment (chimera) being able to bind to an antigen, wherein said chimera comprises a VH and a VL domain comprising
  i) antigen-binding loops derived from a donor immunoglobulin or immunoglobulin fragment (donor) which is able to bind to said antigen, and
  ii) framework regions derived from an acceptor immunoglobulin or immunoglobulin fragment (acceptor), and, optionally,
  iii) further residues from said donor if required for improving antigen-binding,
and wherein the VH domains of said donor and of said acceptor belong to different framework structure subgroups, said method comprising the steps of
  a) comparing the structural features of the VH domains of said acceptor and of said donor;
  b) identifying one or more framework positions in VH where different amino acid residues present in said acceptor and said donor lead to the formation of different framework structure subgroups; and
  c) setting up a stabilized antigen-binding immunoglobulin or immunoglobulin fragment by replacing in the chimeric one or more of the residues present at said positions in the acceptor by those present at said positions in the donor.

In the context of the present application, the following abbreviations are used: "Chimera" is used instead of the expression "chimeric immunoglobulin or immunoglobulin fragment", "donor" instead of "donor immunoglobulin or immunoglobulin fragment", and "acceptor" instead of "acceptor immunoglobulin or immunoglobulin fragment". The term "chimeric" in the context of the present invention refers to a molecule composed of portions from two different molecules. Immunoglobulin fragments according to the present invention may be Fv, scFv, disulfide-linked Fv (Glockshuber et al., 1992; Brinkmann et al., 1993), Fab, (Fab')$_2$ fragments or other fragments well-known to the practitioner skilled in the art, which comprise the variable domain of an immunoglobulin or immunoglobulin fragment. Particularly preferred is the scFv fragment format.

The term "antigen-binding loops" refers to those parts of the variable domain of immunoglobulins or immunoglobulin fragments which are primarily responsible for antigen-binding. Kabat et al. (1979) defined complementarity determining regions (CDRs) as being responsible for antigen-binding based on the degree of variability found in antibody sequences. Later, Chothia and co-workers defined the antigen-binding loops based on structural considerations. Allazikani et al. (1997) review and compare the definitions according to Kabat and Chothia. The term "further residues from said donor if required" refers to the situation that additional residues outside of the antigen-binding loops are grafted onto the acceptor. EP-B1 0 451 216 teaches methods which allow to identify such further residues.

The analysis according to the present invention involves the analysis of contacts between framework residues and the identification of differences in hydrogen-bonding patterns, torsion angles of side chains, changes of the polypeptide main chain conformation and of the tertiary structure. Particularly preferred is the analysis of the residues in framework 1 of the VH domain, and most preferred the analysis of differences caused by different residues in positions H6 to H10, and the consequences of such differences throughout the VH domain by interactions with further VH domain residues and correlated sequence and conformational differences[31]. Differences in positions H6 to H10 can be used to define different framework structure subgroups.

In the context of the present invention, a numbering scheme is used in accordance with Kabat et al. (1979). Thus, the number does not necessarily correspond to the actual position in the sequential order of residues in a VH or VL chain, but indicates a relative position corresponding to the sequences in the Kabat database of antibody sequences. "H" refers to positions in VH, "L" to positions in VL. Thus, H6 is residue number 6 according to Kabat in VH.

In a preferred embodiment, the method of the present invention further comprises that step a) is performed by analyzing VH domain structures and/or structure models. Data on VH domain structures can be obtained from NMR studies, or preferably from X-ray structures of immunoglobulins or immunoglobulin fragments. Homology models can be generated by using different molecular modelling software packages available and well-known to the practitioner skilled in the art. Preferably, the molecular modelling software Insight97 (Biosym/MSI, modules Homology, Biopolymer and Discover) is used.

Preferably, the sequence identity of VH domains used for structure analysis and/or structure modelling show a high degree of sequence identity to the corresponding VH domain of said donor or acceptor. Preferably, said sequence identity is larger than 75%, and most preferably, larger than 80%.

Further preferred is a method, wherein said one or more framework positions comprise H6.

Yet further preferred is a method, wherein said one or more framework positions comprise H9.

In another embodiment, the present invention relates to a method, wherein said acceptor is the human anti-c-ErbB2 scFv fragment 4D5 (SEQ-ID No. 1).

The anti-c-ErbB2 scFv fragment 4D5 has been described hereinabove.

In a further preferred embodiment, said donor is the anti-EGP-2 scFv fragment obtained from the murine hybridoma MOC31 (SEQ-ID No. 2).

The murine hybridoma MOC31 and the anti-EGP-2 scFv fragment obtained therefrom is described hereinabove and in the example.

In a yet further preferred embodiment of the present invention, said one or more framework positions in VH are H6, H9, H18, H20, H38, H63, H82 and H109 (numbering according to Kabat et al. (1979), see above).

In a still further embodiment, the present invention relates to a method, wherein said stabilized antigen-binding immunoglobulin or immunoglobulin fragment is the is the anti-EGP-2 scFv fragment 4D5MOC-B (SEQ-ID No. 3).

In another embodiment, the present invention relates to an antigen-binding immunoglobulin or immunoglobulin fragment stabilized according to a method of the present invention.

In a most preferred embodiment, said antigen-binding immunoglobulin or immunoglobulin fragment is the anti-EGP-2 scFv fragment 4D5MOC-B (SEQ-ID No. 3).

In yet another embodiment, the present invention relates to a modified antigen-binding immunoglobulin or immunoglobulin comprising the variable domain of an antigen-binding immunoglobulin or immunoglobulin fragment stabilized according to a method of the present invention, said modification being a) the conversion to a different immunoglobulin fragment or full immunoglobulin, and/or b) the attachment of additional moieties, such as detection or purification tags, reporter molecules, effector molecules, association domains or combinations thereof. Said modified immunoglobulin fragments according to the present invention may be an Fv, scFv, disulfide-linked Fv, Fab, (Fab')$_2$ fragments or other fragment, or a full immunoglobulin such as IgG, IgA, IgM well-known to the practitioner skilled in the art, which comprise the variable domain of said stabilized immunoglobulin or immunoglobulin fragment and which is different from the immunoglobulin or immunoglobulin fragment format of said stabilized immunoglobulin or immunoglobulin fragment.

Particularly preferred are moieties which have a useful therapeutic function. For example, the additional moiety may be a toxin molecule which is able to kill cells (Vitetta et al., 1993). There are numerous examples of such toxins, well known those skilled in the art, such as the bacterial toxins *Pseudomonas* exotoxin A, and diphtheria toxin, as well as the plant toxins ricin, abrin, modeccin, saporin, and gelonin. By fusing such a toxin to an immunoglobulin or immunoglobulin fragment according to the present invention, the toxin can be targeted to, for example, diseased cells, and thereby have a beneficial therapeutic effect. Alternatively, the additional moiety may be a cytokine, such as IL-2 (Rosenberg & Lotze, 1986), which has a particular effect (in this case a T-cell proliferative effect) on a family of cells. In a further preferred embodiment, the additional moiety is at least part of a surface protein which may direct the fusion protein to the surface of an organism, for example, a cell or a phage, and thereby displays the immunoglobulin or immunoglobulin fragment partner. Preferably, the additional moiety is at least part of a coat protein of filamentous bacteriophages, most preferably of the geneIII protein. In a further embodiment, the additional moiety may confer on its immunoglobulin or immunoglobulin fragment partner a means of detection and/or purification. For example, the fusion protein could comprise the modified immunoglobulin or immunoglobulin fragment and an enzyme commonly used for detection purposes, such as alkaline phosphatase (Blake et al., 1984). There are numerous other moieties which can be used as detection or purification tags, which are well known to the practitioner skilled in the art. Also provided for by the invention are additional moieties such as the commonly used c-myc and FLAG tags (Hopp et al., 1988; Knappik & Plückthun, 1994).

By engineering one or more fused additional domains, immunoglobulin or immunoglobulin fragment can be assembled into larger molecules which also fall under the scope of the present invention. To the extent that the physical properties of the immunoglobulin or immunoglobulin fragment determine the characteristics of the assembly, the present invention provides a means of increasing the stability of such larger molecules. For example, mini-antibodies (Pack, 1994) are dimers comprising two scFv fragments, each fused to a self-associating dimerization domain. Dimerization domains which are particularly preferred include those derived from a leucine zipper (Pack & Plückthun, 1992) or helix-turn-helix motif (Pack et al., 1993).

All of the above embodiments of the present invention can be effected using standard techniques of molecular biology known to anyone skilled in the art.

In a further preferred embodiment, said modification is the attachment of a penta- or hexa-histidin-tag.

Peptides comprising at least five histidine residues (Hochuli et al., 1988) are able to bind to metal ions, and can therefore be used for the purification of the protein to which they are fused (Lindner et al., 1992). Vectors such as pIG-6 (see example) encoding a pentahistidin tail may be used to produce such modified immunoglobulins or immunoglobulin fragments. In addition, pIG-6 provides an N-terminal FLAG-tag and a C-terminal c-myc-tag for detection purposes.

Further preferred is a modified fragment wherein said penta- or hexa-histidin-tag is complexed with a 99mTc-tricarbonyl moiety.

The His-tag specific 99mTc labeling method has been described (Alberto et al., 1998). 99mTc-tricarbonyl trihydrate forms very stable complexes with the penta- or hexa-histidine tag. The modified fragments containing a 99mTc-tricarbonyl moiety may be used for radiotherapy or radioimaging approaches.

In a most preferred embodiment, the present invention relates to a modified fragment, comprising the variable domain of the anti-EGP-2 scFv fragment 4D5MOC-B (SEQ-ID No. 3) according to the present invention.

Further preferred are a nucleic acid sequence or nucleic acid sequences encoding an antigen-binding immunoglobulin or immunoglobulin fragment according to the present invention.

Depending on the immunoglobulin or immunoglobulin fragment type, a single nucleic acid sequence, e.g. for encoding an scFv fragment, or two, e.g. for encoding an Fab fragment, or more nucleic acid sequences are required. Preferentially said nucleic acid sequences are comprised in a vector, preferably a vector suitable for sequencing and/or expression. Said vector comprising said nucleic acid sequence or nucleic acid sequences may be comprised in a host cell.

In a further preferred embodiment, the present invention relates to a method for the production of a stabilized antigen-binding immunoglobulin or immunoglobulin fragment according to the present invention comprising the expression of one or more nucleic acid sequences according to the invention encoding said antigen-binding immunoglobulin or immunoglobulin fragment in a suitable expression system.

The expression system may be expression in a suitable host. The host referred to herein may be any of a number commonly used in the production of heterologous proteins, including but not limited to bacteria, such as *E. coli* (Ge et al, 1995), or *Bacillus subtilis* (Wu et al., 1993), fungi, such as yeasts (Horwitz et al., 1988; Ridder et al., 1995) or filamentous fungus (Nyyssönen et al., 1993), plant cells (Hiatt, 1990, Hiatt & Ma, 1993; Whitelam et al., 1994), insect cells (Potter et al., 1993; Ward et al., 1995), or mammalian cells (Trill et al., 1995).

The expression system may be expression in a cell-free translation system, preferably in a coupled in vitro transcription/translation system. Preferably, such a translation is carried out in a prokaryotic translation system. Particularly preferred is an *E. coli* based translation system such as the S-30 *E. coli* translation system. Alternatively, the translation may be carried out in a eukaryotic translation system.

In a further most preferred embodiment, the present invention relates to a pharmaceutical composition containing an antigen-binding immunoglobulin or immunoglobulin fragment according to the present invention and, optionally, a pharmaceutically acceptable carrier and/or diluent.

In a yet further preferred embodiment, the present invention relates to the use of a stabilized immunoglobulin or immunoglobulin fragment according to the present invention, or of a modified immunoglobulin or immunoglobulin fragment according to the present invention for the preparation of a pharmaceutical composition for the treatment of human carcinomas.

Further preferred is the use of the anti-EGP-2 scFv fragment 4D5MOC-B, or of a modified EGP-2-binding immunoglobulin or immunoglobulin fragment according to the present invention for the preparation of a pharmaceutical composition for the treatment of human carcinomas.

In a yet further preferred embodiment, the invention relates to a diagnostic composition containing an antigen-binding immunoglobulin or immunoglobulin fragment according to the present invention.

In a still further preferred embodiment, the invention relates to a diagnostic kit containing an antigen-binding immunoglobulin or immunoglobulin fragment according to the present invention.

Figure 1A:
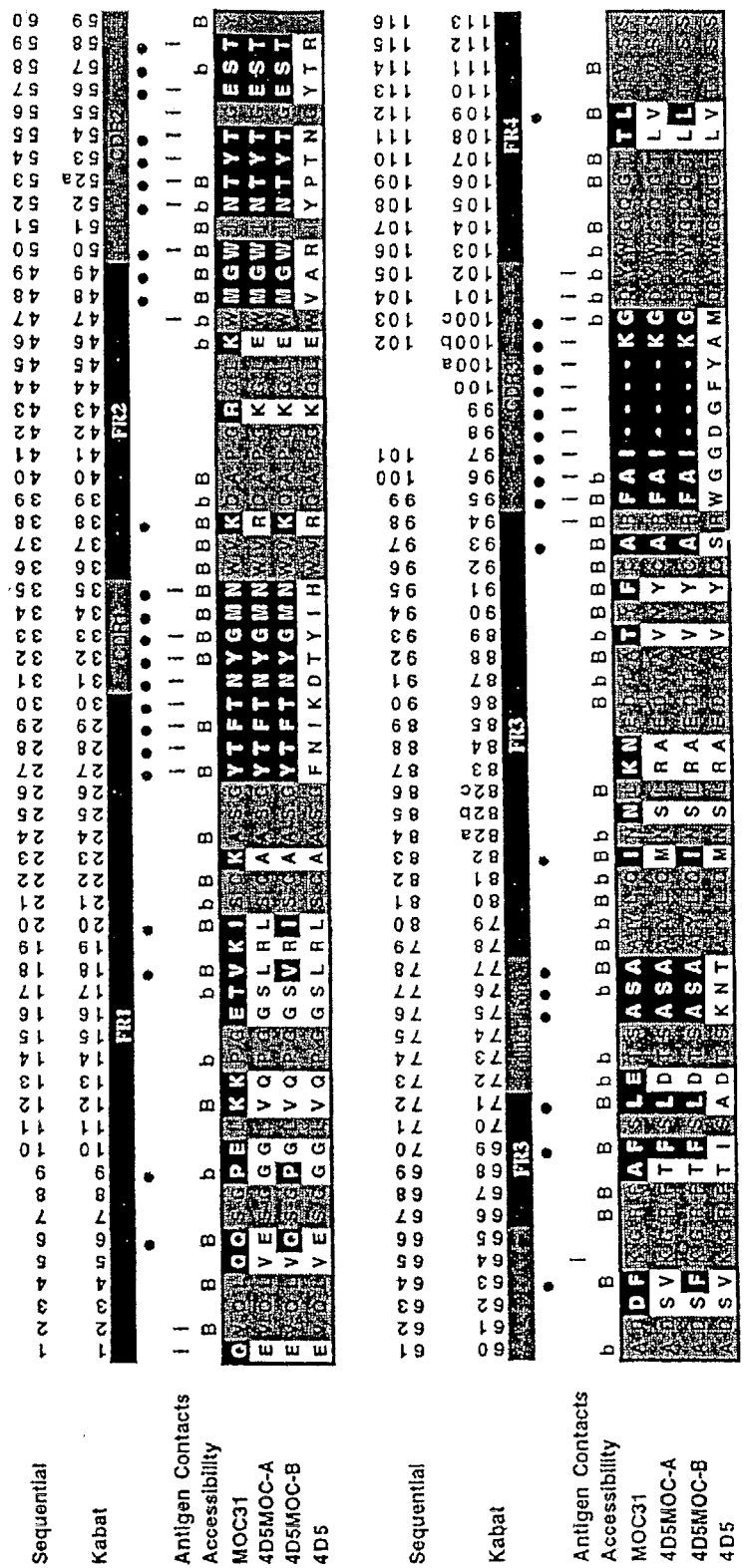
FIG. 1

Sequence alignment of the VL and VH domains of scFv MOC31, 4D5MOC-A, 4D5MOC-B and 4D5: (A) Positions of sequence agreement between MOC31 and 4D5 are indicated by black letters on a gray background, residues which agree with 4D5 but are different from MOC31 by black letters on a white background and residues which agree with MOC31 but not with 4D5 are indicated by white letters on a black background. Residue labels and CDR definitions are according to Kabat (1987). (B) indicates residues buried in the domain core or interface, (b) semiburied residues. (•) and (•) indicate potential antigen contact residues, detected by a large (•, >40%) or small (•>1%) loss of side chain solvent accessible surface upon complex formation, averaged for this position over all different protein-antibody complexes in the PDB database. Model of the scFv fragment 4D5MOC-B: (B) Quaternary structure of the anti-EGP-2 scFv fragment 4D5MOC-B, composed of VL (grey) and VH (white) with transferred potential antigen contact residues of MOC31 (black). The eight additional transferred murine residues in the core of VH are highlighted (black side chains). A space filling model shows 4D5MOC-B in the top view (C) and bottom view (D). Black balls are of murine and white of 4D5 origin, while grey balls are the same in 4D5 and MOC31.

FIG. 2

Result of purification of scFv 4D5MOC-A and 4D5MOC-B. SDS-PAGE under reducing conditions shows the result of the purification of scFv 4D5MOC-A and 4D5MOC-B after IMAC and subsequently performed ion exchange.

[MW standard:phosphorylase b (97.4 kDa); bovine serum albumine (66 kDa); ovalbumine (44 kDa); carbonic anhydrase (29 kDa); trypsin inhibitor (21.5 kDa); lysozyme (14.3 kDa)]

FIG. 3

Binding experiments with 99mTc-labelled 4D5MOC-A and -B (RIA).

(A) Competition RIA of Tc-labelled 4D5MOC-A and 4D5MOC-B on SW2-lung cancer cells with MOC31. Fifty ng radiolabelled scFv fragment were incubated with or without MOC31 (10 µg) or with the same amount of an anti c-erbB2 monoclonal antibody as an irrelevant inhibitor. (B) Binding specificity of 99mTc labelled 4D5MOC-A and 4D5MOC-B on different antigens (500 ng/well).

FIG. 4

Check of Thermal and Serum Stability

Gel filtration over superdex 75 column before and after overnight incubation (20 h) at 37° C. of 4D5MOC-A (A) and 4D5MOC-B (B). Determination of remaining immunoactivity of $^{99m}$Tc-labelled anti-EGP-2 scFv fragments before (C) and after overnight (D) incubation in human serum at 37° C. by incubation by Lindmo-assay[29].

The example illustrates the invention.

EXAMPLE

Material and Methods

Mammalian Cell Lines

The human small cell lung carcinoma cell line SW2, kindly provided by Dr. S. D. Bernal (Dana Farber Cancer Institute, Boston, Mass., USA) and breast cancer cell line SK-BR-3 (#HTB 30, American type culture collection, Rockville, Md.) were maintained in RPMI 1640 (Hyclone, Europe Ltd.) based medium supplemented with 10% fetal calf serum (Gibco, Grand Island, N.Y.) and grown at 37° C. under an atmosphere of 5% $CO_2$. The breast cancer cell line SK-OV-3 (#HTB 77, American type culture collection, Rockville, Md.) was grown in RPMI 1640, supplemented with EGF (10 ng/ml) and insulin (5 ng/ml).

Epithelial Glycoprotein-2 (EGP-2) and Single-Chain Fv Fragments

The human epithelial glycoprotein-2 was produced as a recombinant soluble protein (M1-F259) with an six-histidine C-terminal tag by use of the expression vector pBB4/GA-733-2 in the baculovirus expression system (Invitrogen). The anti-EGP-2 scFv fragment (scFv MOC31) was assembled from mRNA isolated from the murine hybridoma cell line MOC31[1] by using a reengineered phage display system described before[16]. The single-chain Fv fragment from the human anti-c-erbB2 antibody 4D5 had been constructed from the Fab fragment (Carter et al,) and had been used in several studies before[21,20].

Molecular Modeling/Construction of Graft

A homology model of the anti-EGP-2 scFv fragment was generated using the molecular modelling software Insight97 (Biosym/MSI, modules Homology, Biopolymer and Discover). The $V_L$ domain model was based on the x-ray structures of the mouse Fab fragment JEL103 (22, Brookhaven Database entries 1mrc, 1mrd, 1mre and 1mrf, 2.3%-2.4% resolution, 76% sequence identity to MOC31), the $V_H$ domain model was based on the structure of an anti-neuraminidase Fab ([23,24], pdb entries 1nca, 1ncb, 1ncc and 1ncd, 2.5% resolution, 85% identity) and the CDR H3 conformation of the anti-choleratoxin Fab TE33 ([25], pdb entry 1tet, 2.3% resolution, 82% identity). The MOC31 domain models were superimposed on the crystal structure of the Fv of humanized 4D5 version 8 ([26], pdb entry 1fvc, 2.2% resolution, $V_L$: 55% identity, $V_H$: 50% identity to MOC31). Potential antigen contacts were identified by comparing the side chain solvent accessible surface of known antibody-protein complexes in the presence and absence of the ligand using the program naccess (S. Hubbard and J. Thornton, 1992, http://sjh.bi.umist.ac.uk/naccess.html). The models were checked for possible steric conflicts, potential antigen contacts and residues which might have an indirect influence on CDR conformations, resulting in the hybrid scFv 4D5MOC-A. In a second construct, scFv 4D5MOC-B, 8 key residues in the core of $V_H$ were retained from the MOC31 sequence instead of changing them to the 4D5 sequence in order to preserve the structural subtype of the MOC31 $V_H$ framework.

The designed sequences for both variants were backtranslated (GCG-package) and the fragments were constructed by gene synthesis[27] from eight overlapping oligonucleotides for $V_L$ and ten for the two different variants of $V_H$, in the orientation $V_L$-linker-$V_H$. The length of the used oligonucleotides was between 40 bp and 78 bp. Each domain was produced separately and cloned blunt-ended into the pBluescript vector (Stratagene) and was subsequently sequenced. $V_L$ and $V_H$ domains were then cloned into the expression vector pIG6 (Ge et al., 1995). A 24-mer non-repetitive linker TPSHNSHQVPSAGGPTANSGTSGS[28] was then introduced by cassette mutagenesis via AflII and BamHI restriction sites.

Expression and Purification of Single-Chain Fv Fragments

For periplasmic expression of the c-erbB2 binding scFv fragment 4D5 and the EGP-2 binding scFv fragments 4D5MOC-A and 4D5MOC-B, the pIG6 vector was used, while the pAK400 vector[16] was used for the expression of scFv MOC31. For large scale production, the E. coli strain SB536 (Bass et al. 1996) was used. One liter of dYT containing 1% glu and Ampicillin (30 μg/ml) in a 5 l shake flask was inoculated with 30 ml of overnight culture. When the culture reached an $OD_{550}$ nm of 0.5, scFv production was induced with a final concentration of 1 mM isopropyl-D-galactopyranoside (IPTG; Boehringer Mannheim) for three to four hours at 24° C. The final OD was five—six for 4D5, 4D5MOC-A 4D5MOC-B and four for scFv MOC31. The harvested pellet was stored at −80° C.

For purification the pellet from 1 liter culture was re-suspended in 20 mM Hepes pH 7.0, 30 mM NaCl and lysed with two cycles in a French Pressure Cell press (SLS instruments Inc., Urbana Ill., USA). The cleared lysate was centrifuged in a SS-34 rotor at 48246 g at 4° C. and filter sterilized. All single-chain Fv fragments were purified over a $Ni^+$-IDA-column and HS/M-4.6/100-ion exchange column, coupled in-line on a BIOCAD-System (Perseptive BioSystem-Inc.) as described previously (Plückthun 1996, book chapter). After loading the lysate on the $Ni^+$-IDA-column the column was washed with 20 mM Hepes pH 7.0, 500 mM NaCl, and in a second step with 20 mM Hepes pH 7.0, 40 mM imidazole before bound protein was eluted with 200 mM imidazole, pH 7.0. The eluate was loaded directly on the HS/M-4.6/100-ion-exchange-column, and the specifically bound protein was eluted with a salt gradient from 0 to 500 mM NaCl in 20 mM Hepes pH 7.0. The fraction containing the antibody fragment was dialyzed against an excess of PBS and concentrated to 1 mg/ml using a 10 kDa cut-off filter (Ultrafree-MC low protein binding, Millipore) by centrifugation at 4000 g at 4° C. For the anti-EGP-2 scFv fragment MOC31 it was necessary to perform a preparative gel filtration over a Superdex75 column (Pharmacia) as the third purification step which lowered the final yield again ten-fold. The result of the purification was checked on a 12.5% SDS-PAGE under reducing conditions. The molecular weights of all purified scFvs were checked by mass spectrometry.

His-Tag Specific [99m]Technetium Labeling of Single-Chain Fv Fragments

[99m]Tc-tricarbonyl trihydrate (Alberto et al., 1998), forms very stable complexes with the penta- or hexahistidine tag, therby making dual use of the His tag which is present for immobilized metal affinity chromatography (IMAC) purification. The scFv fragments (1 mg/ml) were mixed with one-third volume of [99m]technetium-tricarbonyl (30 mCi/ml) in buffer and one-third volume of 0.5 M MES pH 6.2 and incubated for thirty minutes at 37° C. ScFv MOC31 was labelled for 30 min at 30° C. at a protein concentration of 400 μg/ml to avoid precipitation. The reaction mixture was desalted over a Fast desalting column (Pharmacia) equilibrated with PBS.

Aliquots of the collected fractions were measured in a scintillation counter to identify the fractions with the labelled protein.

Analytical Gel Filtration

Analytical gel filtration was performed with the Smart system (Pharmacia), using a Superdex 75 column. All measurements were carried out in PBS buffer containing 0.005% Tween-20. The scFv fragments were injected at a concentration of 1 mg/ml in a volume of 15 μl before and after overnight incubation for 20 h at 37° C. The column was calibrated in the same buffer with alcohol dehydrogenase (150 kDa), bovine serum albumin (66 kDa), carbonic anhydrase (29 kDa) and cytochrom c (12.4 kDa) as molecular mass standards.

Binding Specificity

The binding specificity of the different scFv fragments was tested by competition with the monoclonal antibody MOC31. Fifty ng radiolabelled scFv 4D5MOC-A or 4D5MOC-B were incubated with $0.5 \times 10^6$ SW2 cells in 200 μl PBS/1% BSA after pre-incubation with or without the mAb MOC31 (10 μg) or with the same amount of an anti-c-erbB2 monoclonal antibody as an irrelevant competitor for 30 min at 4° C. In three washing steps cells were centrifuged at 1000 g for 5 min at 4° C., the supernatant discarded and the cells re-suspended in PBS/1% BSA. The remaining radioactivity was then measured in a scintillation counter. In a further binding experiment both scFv fragments (50 ng) were incubated with different antigens, coated (500 ng/well) on a 96 well microtiter plate, to check for cross-reactivity. The wells were washed three times with PBS/1% BSA and the radioactivity was determined.

$K_D$-Determination by RIA and Surface Plasmon Resonance (Biacore)

The binding affinity of the $^{99m}$Tc labelled single-chain Fv fragments was determined on SW2 cells in a radio-immunoaffinity assay (RIA). SW2 ($0.5 \times 10^6$) cells were incubated with increasing amounts of single-chain Fv fragment (100 μM-30 nM) for 1 hour at 4° C. For estimation of nonspecific binding control samples of cells were pre-incubated with a 100-fold excess of unlabelled single-chain Fv fragment for 1 h at 4° C. The bound fraction of single-chain Fv fragment was determined in a scintillation counter. Each obtained value represents the mean of two samples. Counts per minutes (cpm) were plotted against the nanomolar concentration of single-chain Fv fragment and fitted with the non-linear regression function.

Kinetic rate constants were determined by surface plasmon resonance (SPR) with a BIAcore instrument. Recombinant soluble EGP-2-antigen was covalently coupled to a CM-5 sensor chip via free amine groups resulting, in a surface coverage of 350 resonance units. Single-chain Fv fragments were injected in increasing concentrations (0.1 nM-4 μM) at a flow rate of 30 μl/min of degassed PBS/0.005% Tween-20. Association and dissociation rate constants were calculated from the sensorgram the by a global curve fit using the BIAevaluation 3.0 software (Pharmacia).

Serum Stability of Radiolabelled scFv at 37° C.

The fraction of single-chain Fv fragments remaining immunoactive after radioactive labeling was determined as described previously[29]. Samples containing different numbers of cells ($0.625 \times 10^6$–$10 \times 10^6$) were incubated in 100 μl with fifty ng of radiolabelled scFv fragments for 1 h at 4° C. on a shaker. Unspecific binding was determined on control samples of cells pre-incubated with a 100-fold excess of unlabelled scFv fragments in PBS/1% BSA. After three washing steps, the amount of bound scFv fragments was then determined in a scintillation counter. Each reported value represents the mean of the result of two samples. For calculation of the immunoactivity total counts per minute (cpm) were divided by measured cpm value for bound protein and then plotted against inverse cell number and fitted by linear regression. The inverse y-intercept in percent gives the percentage bioactive single-chain Fv fragments. To estimate the stability of the different radiolabelled single-chain Fv fragments in serum, the molecules were incubated overnight (20 h) in human serum at 37° C., at a final concentration of 17 μg/ml and the remaining immunoactivity determined in the Lindmo assay.

In Vivo Characterization—Clearance and Biodistribution

Blood clearance studies were performed with eight-week-old, tumor free female CD1 nude mice. Each mice received i.v. 300 μCi of $^{99m}$Tc labelled scFv 4D5MOC-B. After 7.5, 15, 30, 60, 120, and 240 minutes following injection, blood samples were taken, and $t_{1/2}\alpha$ and $t_{1/2}\beta$ value was calculated from the measured radioactivity. Biodistribution study of $^{99m}$Tc labelled scFv fragment 4D5MOC-B was done in six-week-old CD1 nude mice bearing 13 days old SW2 xenografts (40-80 mg). Each mouse of three groups of four mice received 30 μg radiolabelled scFv (300 μCi). Biodistribution analysis of $^{99m}$Tc labelled scFv MOC31 was performed in seven-week-old Black-nude mice (strain bl6 Uwe: B16??) carrying ten-day-old SW2-xenografts (10-40 mg). Each mouse of three groups of three mice was administered 5 μg $^{99m}$technetium-labelled scFv MOC31 (85 μCi). Anti-fluorescein binding scFv FITC-E2 was used as an nonspecific control antibody. The mice were killed at 1, 4 and 24 hours after injection. Tissue and organs were removed and assessed for activity using a gamma-counter. The biodistribution analysis with $^{99m}$Tc labelled scFv 4D5 was described recently (Waibel et al., 1999).

Results

Molecular Modeling—Construction of Graft

We have constructed the scFv fragment of MOC31 using standard phage display methodology[16], determined its functionality and demonstrated a rather high affinity to its antigen EGP-2 (Table 1), consistent in sequence and properties with an independently constructed scFv MOC31[30]. Surprisingly, the in vivo localization of this scFv was hardly distinguishable from a control scFv without EGP-2 specificity and essentially the scFv MOC31 did not localize to a xenografted tumor (table 2). We therefore hypothesized that this protein is not stable enough and designed two more stable variants, first, by grafting the loops to a well-characterized stable framework and second, additionally changing several residues in the interior of one of the variable domains. As the recipient framework, we chose the humanized version of 4D5[19], itself an product of a grafting exercise. This framework consists essentially of a heavy chain variable domain derived from the germline IGHV 3-66 (IMGT), VH 3-18 (Vbase), Locus DP 3-66 (DP-86) and a the kappa light chain variable domain derived from germline IGKV 1-39 (IMGT), VK 1-1 (Vbase), locus DP O12.

A homology model of MOC31 was built and compared to the X-ray structure of the human 4D5 version 8 Fv fragment (pdb entry 1fvc). Potential antigen contact residues were identified by an analysis of antibody-protein antigen complexes in the Brookhaven Protein Database (FIG. 1A). Based on this information, rather than on Kabat definitions, it was decided which residues to take from the 4D5 framework and which ones to take from the MOC31 sequence. The resulting graft did thus not strictly follow the CDR definition according to Kabat et al. (1979) or Chotia (see Allazikani et al., 1997), but includes two residues (L64 and L66) which determine the conformation of the "outer loop" of $V_L$ (residues L66-L71). The tip of this loop was shown to contact the antigen in some complexes, and an influence of this loop on the conformation of CDR L1 could not be excluded. Residue L66 usually is Gly in kappa light chains and assumes a positive φ angle. If this residue is replaced by a non-Gly residue (Arg in 4D5), the outer loop assumes a different conformation, bending away from the domain. In $V_H$, in addition to CDR H1, residues H27 to H30 were included, while some residues at the base of CDR2 were omitted (H62 and H63), despite being part of CDR H2 according to CDR definitions (Kabat et al. (1979); Allazikani et al., 1997), and several residues in the "outer loop" of $V_H$, sometimes referred to as CDR4, were included (residues H69, H71, H75-H77), resulting in the construct 4D5MOC-A (FIG. 1A).

Analysis of the conformations of $V_H$ domain frameworks revealed that these can be classified according to their framework conformation into 4 distinct subgroups. The conformational differences are most noticeable in framework 1 (FR1), particularly in positions H7-H10, although correlated sequence and conformational differences are found throughout the molecules, involving several core residues[31]. These conformational changes are probably caused by the different hydrogen bonding patterns which the fully buried Glu H6 (as in 4D5) or Gln H6 (as in MOC31) establishes in the core of the domain, and are further influenced by the nature of residue H9 (Pro, Gly or other residues) 32. Saul and Poljak (1993) reported correlated structural changes affecting residues H9, H18, H82, H67 and H63 which relay the effects of changes in FR1 conformation across the domain core to the base of CDR2, thus potentially enabling them to potentially affect antigen binding.

According to this classification, MOC31 belongs to a different subclass than 4D5. Since we did not know to what extent these framework classes affect the functionality of a loop graft, we decided to test this aspect experimentally. While in construct 4D5MOC-A the $V_H$ domain framework was changed to the 4D5 subtype, 4D5MOC-B fully retains the MOC31 core packing as well as the conformationally critical residues H6 and H9. To achieve this, eight additional framework residues of the anti-EGP-2 single-chain Fv fragment sequence (H6, H9, H18, H20, H38, H63, H82 and H109) had to retain the MOC31 sequence. All of these changes are located in the lower half of the scFv (FIG. 1), and with the exception of the Gly to Pro substitution in position H9, are buried in the core of the domain. They are therefore not expected to affect the immunogenicity of the construct.

For introduction of the AflII restriction site it was necessary to modify the C-terminal sequence of the $V_L$-domain in all constructs from EIKRA to ELKRA, which should not affect the domain structure.

Expression and Purification of scFv Constructs

Figure 2:
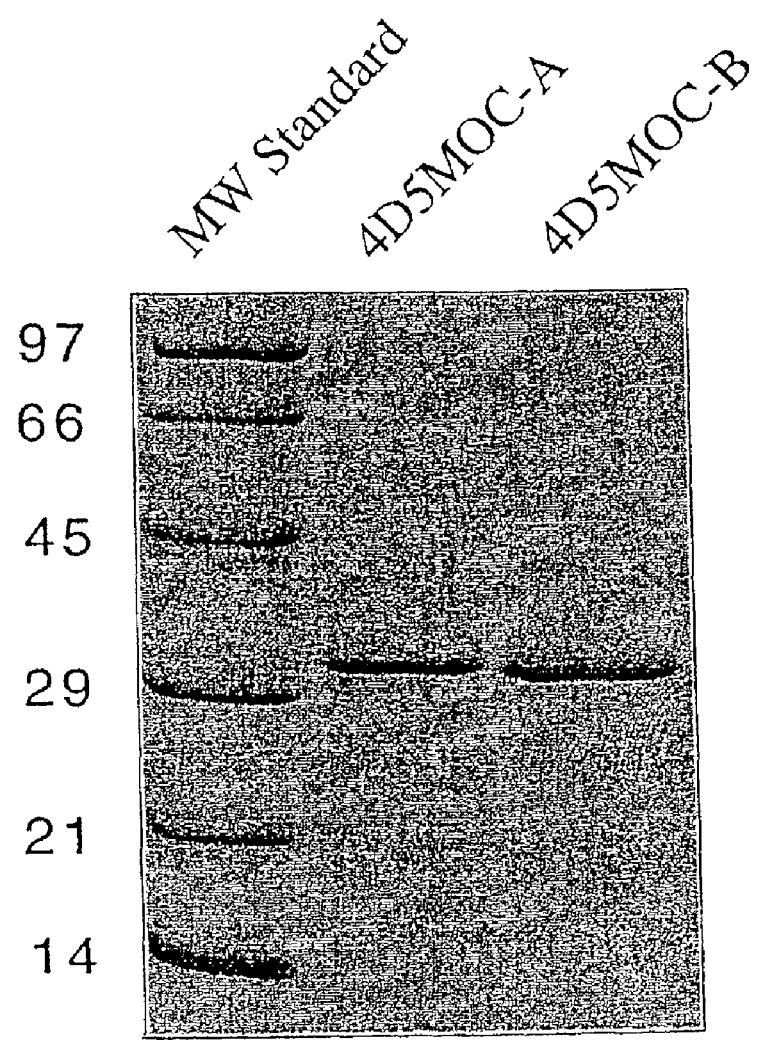

For scFv 4D5 usually 1-2 mg pure protein could be purified from one liter of culture, while for scFv MOC31 the yield was much lower. After two steps of purification scFv MOC31 yielded only 200 μg at a purity of about 70%. Coexpression of skp[33] increased the yield to 600 μg, but there was still a 20 kDa degradation product present. The graft variant scFv 4D5MOC-A could be purified to a yield of 400 μg and 4D5MOC-B to 1 mg at a purity over 95%. Both single-chains Fv fragments could be concentrated to 1 mg/ml and were analyzed on a reducing SDS-PAGE (FIG. 2). Mass spectrometry of both molecules showed the expected molecular weight of 29,855 Da for scFv 4D5MOC-A and 29,897 Da for scFv 4D5MOC-B.

Binding Specificity

Figure 3A:
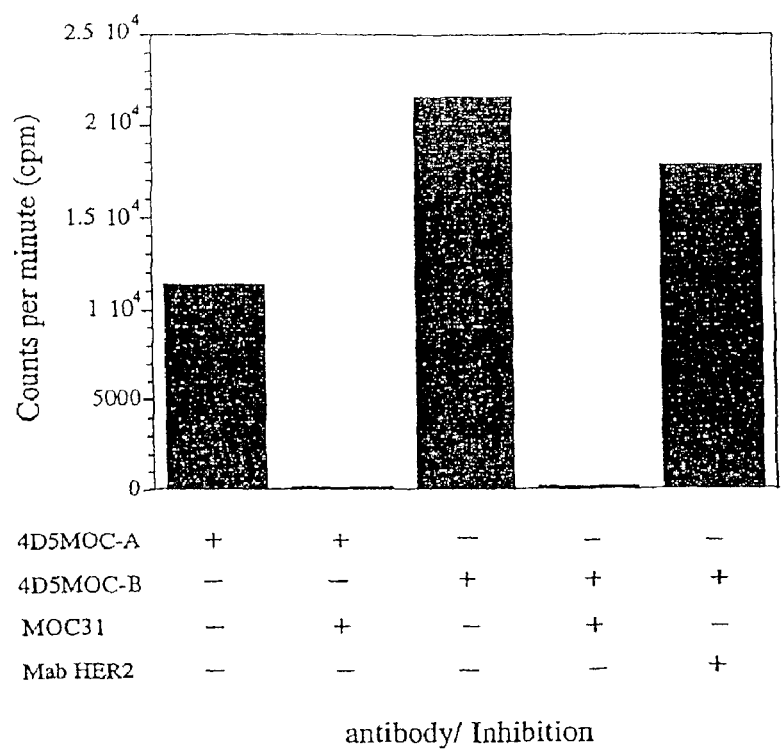
Figure 3B:
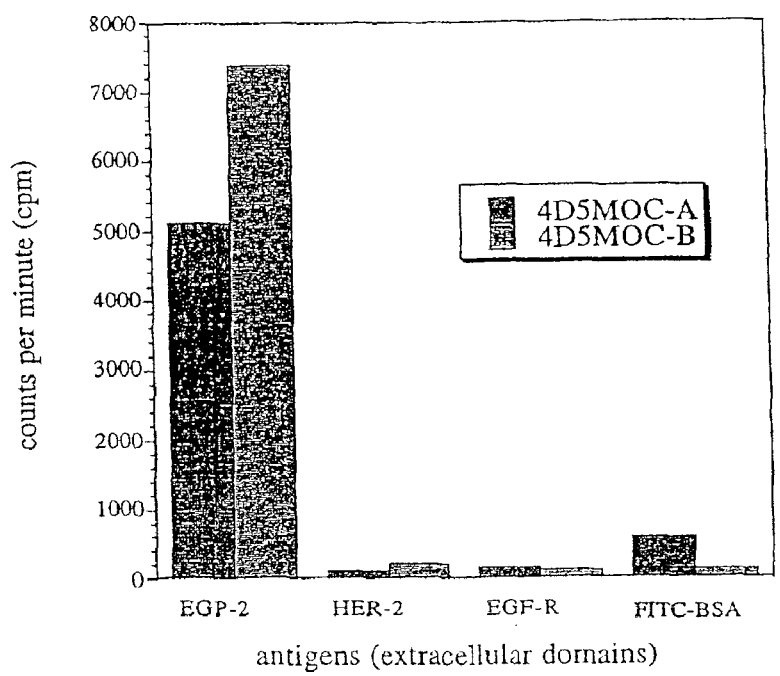

The transfer of the anti-EGP-2 binding specificity of scFv MOC31 onto the framework of scFv 4D5 was shown to be successful for both variants, 4D5MOC-A and 4D5MOC-B, by binding competition of the radiolabelled graft variants to EGP-2 overexpressing SW2 cells. Only the monoclonal antibody MOC31 could inhibit binding of the graft variants, whereas an irrelevant control antibody did not compete (FIG. 3A). No cross-reactivity of the grafted molecules were seen when incubated on c-erbB2 or EGF-receptor (extracellular domain) (FIG. 3B).

Determination of $K_D$

High-affinity binding with long residual time on the specific target antigen is regarded as one of the most important characteristics of antibodies for tumor targeting. To ensure that binding affinity was conserved in the grafting experiment dissociation constants of the radiolabelled single-chain Fv fragment were determined on cells in a radioimmunoactivity assay (RIA). The graft variants showed specific and similar binding behavior comparable to the parent anti-EGP-2 single-chain Fv fragment in the nanomolar range (Table 1).

Binding kinetics of unlabelled scFv fragments to immobilized EGP-2 were also analyzed by surface plasmon resonance (Table 1) in the BIAcore instrument (Pharmacia). To minimize rebinding effects which could lead to an underestimation of the off-rates, we used low density coating and high flow rate. ScFv MOC31 showed stable binding on its target with a half-life of about 38 min consistent with an independent determination (half-time of 33 min) 30. The $k_{off}$ values of scFv 4D5MOC-A and 4D5MOC-B were very similar to the parent scFv MOC31 (Table 1), indicating that the full transfer of the binding properties of scFv MOC31 on the 4D5-framework was successful.

Analytical Gel Filtration and Test of Thermal Aggregation

For many applications of scFvs it is crucial to concentrate these molecules and to incubate them at elevated temperatures. The biophysical behavior of these molecules is then often the threshold for their applicability in vivo. Therefore we tested the aggregation behavior of the scFvs at high concentrations and elevated temperatures. While 4D5, 4D5MOC-A and 4D5MOC-B could be concentrated to 1 mg/ml by ultrafiltration, the MOC31 scFv precipitated at concentrations above 400 μg/ml. At this concentration, about 10% of the total protein eluted as high molecular weight aggregates on analytical gel filtration with the Smart gel filtration system (Pharmacia) on a Superdex 75 column. Almost 90% of the protein eluted at a volume of 1.27 ml as expected for the monomeric species. However, already within 30 min at 37° C., approximately 85% of the protein precipitated. The remaining 15% soluble protein eluted as a monomeric species (data not shown).

Figure 4A:
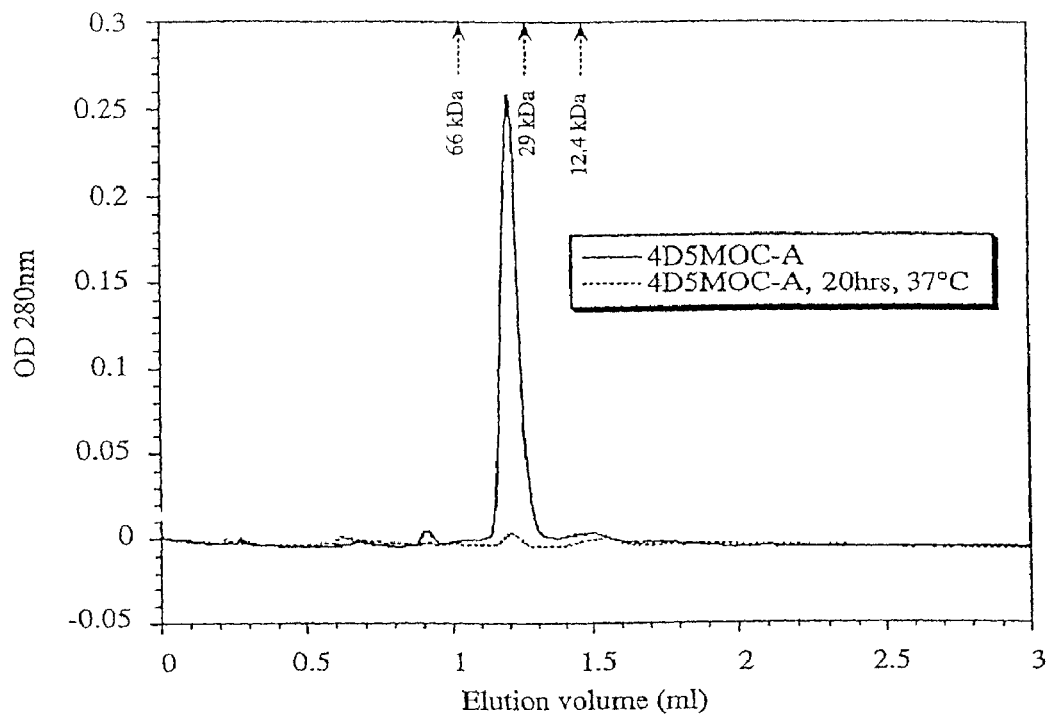
Figure 4B:
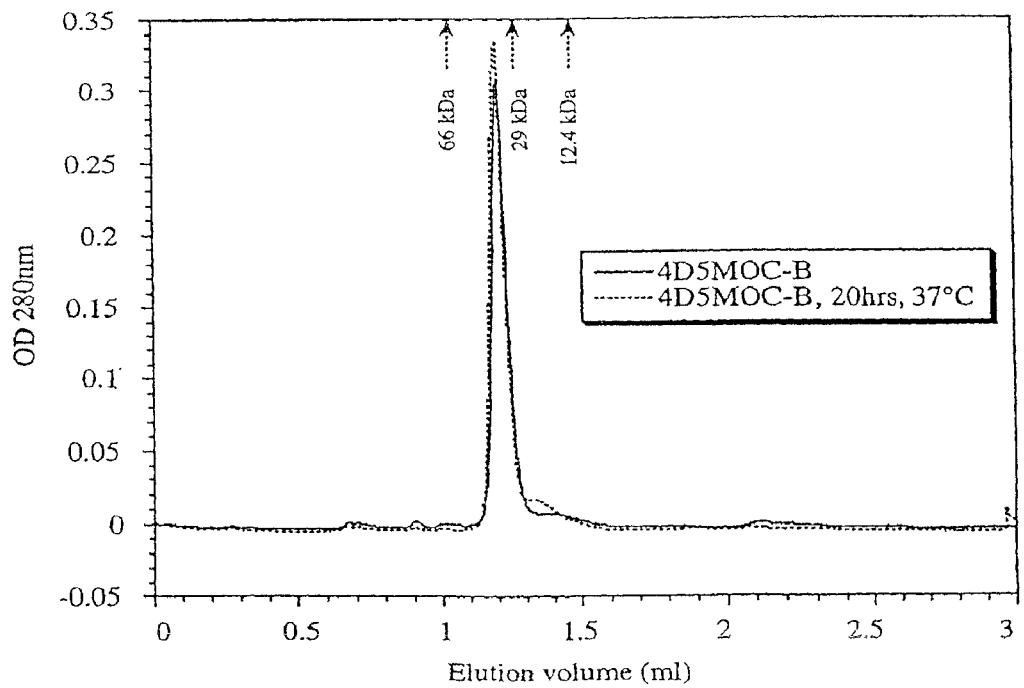

The two grafted variants 4D5MOC-A and 4D5MOC-B eluted at a volume of 1.20 ml, corresponding to a molecular weight of 30 kDa, indicating that both single-chain Fv fragments exist as monomers at a concentration of 1 mg/ml. Although 4D5MOC-A precipitated more slowly than MOC31, overnight incubation in PBS at 37° C. for 20 hrs and subsequent gel filtration showed nearly no eluted protein (FIG. 4A). Incubated under the same conditions, 4D5MOC-B still eluted as a symmetric peak at a volume of 1.20 ml (FIG. 4B), indicating a large difference in intrinsic (thermal) stability of the two variants. Most importantly, 4D5MOC-B, was thereby shown to have the biophysical properties required for in vivo application.

His-Tag Specific $^{99m}$Technetium-Labeling

The single-chain Fv fragments were labelled with $^{99m}$Tc, using a new method in which $^{99m}$Tc-tricarbonyl-trihydrate is stably bound to the C-terminal penta- or hexahistidine tag of recombinant proteins (Waibel et al, 1999). All scFv fragments, except the original scFv MOC31, could be labelled at 37° C. and at a protein concentration of 1 mg/ml, resulting in 30-40% of the initial $^{99m}$Tc incorporated, giving a final specific activity of 300-400 mCi/ml. For the aggregation-prone scFv MOC31, the incubation temperature had to be lowered to 30° C. and the maximal possible protein concentration was 400 µg/ml, resulting in a decreased incorporation yield (25% of total Tc, 250 mCi/ml).

Determination of Immunoactivity After Incubation in Serum at 37° C.

Figure 4C:
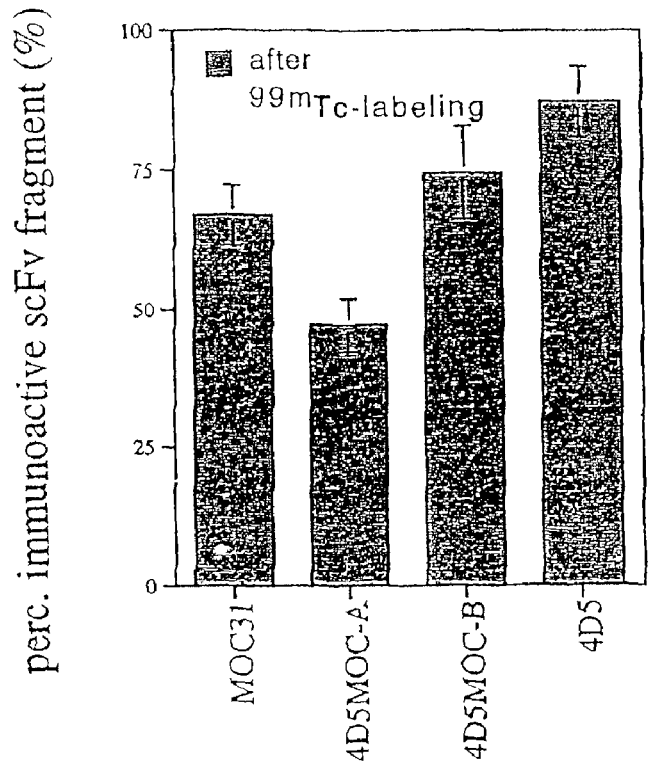
Figure 4D:
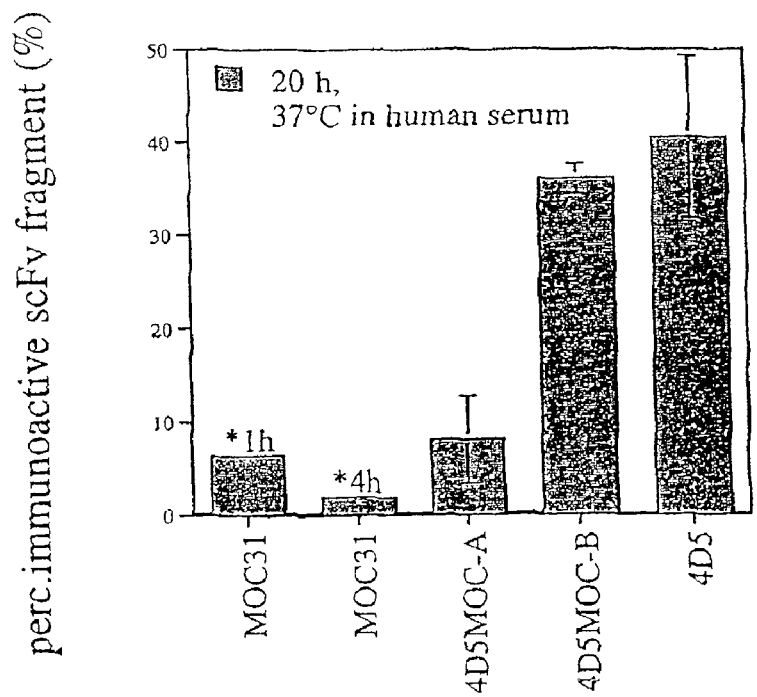

We determined the fraction of scFv molecules still active after $^{99m}$Tc labeling (FIG. 4C)[29] and after incubation of the labelled fragments in human serum for 20 h at 37° C. (FIG. 4D). For scFv MOC31, we found 67%±5.4 of the protein still active if the labeling reaction was performed at 30° C. The other fragments showed 47.25%±4.9 active for scFv 4D5MOC-A, 74.5%±8.3 for scFv 4D5MOC-B and 87.3%±6.4 for scFv 4D5, all labelled at 37° C. To test serum stability, the scFv fragments (17 µg/ml) were incubated in human serum at 37° C. for 20 hours and the remaining immunoactivity determined. ScFv MOC31 was found to be completely inactive after overnight incubation, therefore earlier time points were measured. Already after 1 h, the activity had dropped to 6.32%±0.17 (9.4% of the initial immunoactivity). After 4 h, only 1.95%±0.175 (2.9%) remained active. In contrast, the activity of 4D5MOC-A dropped from 47.25%±4.9 to 8.1%±4.7 (17.1% of the initial value) over 20 h, that of scFv 4d5MOC-B from 74.5%±8.3 to 36%±1.6 (48.3%) and that of scFv 4D5 from 87.3%±6.4 to 40.45%±8.75 (46.3%), confirming the different thermal stabilities found in the gel filtration assay.

In Vivo Characterization—Clearance and Biodistribution

Biodistribution studies were then performed for scFv $^{99m}$Tc-labelled scFvs MOC31, 4D5, 4D5MOC-A and 4D5MOC-B. For scFv MOC31 we were unable to get a tumor-to-blood ratio higher than 0.92 after 1 h, 4 h and 24 h (n=3, each time point). After 24 h the total dose at the tumor was 1.24% ID/g tissue, but also 1.34% ID/g in the blood, which was very high in comparison to the 3-5 fold lower values usually found in the blood after 24 h with that labeling method (Table 2). In contrast, the biodistribution of $^{99m}$Tc labelled scFv 4D5 gave a tumor-to-blood ratio of 8.3 after 24 h with a total dose of 1.5% ID/g on SK-OV-3 cells (Waibel et al., 1999), similar results were reported for the anti-c-erbB2 scFv C6.5[34]. For 4D5MOC-A we found after 24 h only a weak enrichment with a total dose of 0.84% ID/g and a tumor-to-blood ratio of 1.95 (Table 3), while the in vivo application of scFv 4D5MOC-B in SW2-tumor-bearing mice resulted in a tumor-to-blood ratio of 5.25 after 24 h with a total dose of 1.47% ID/g at the tumor. The maximal dose at the tumor was measured after 4 h with 1.82% ID/g, which then decreased very slowly, reflecting fast and stable binding of scFv 4D5MOC-B to the antigen (Table 3). For the nonspecific anti-fluorescein control scFv FITC-E2[15] no enrichment at the tumor site was found (Table 4).

Clearance studies revealed scFv 4D5MOC-B as a very rapid clearing molecule with a $t_{1/2}\alpha$=6 min and $t_{1/2}\beta$=228 min. The comparison with scFv 4D5 with a measured $t_{1/2}(\alpha)$=7.5 min shows that the excellent clearing behavior, which is a prerequisite for the achievement of high tumor-to-blood-ratios is not lost by the loop grafting.

Discussion

It has been reported that indium-DTPA-labelled mAb MOC31 localized to primary tumor and metastases in a clinical trial with small cell lung cancer patients, but it was not superior to other diagnostic methods e.g. computer-tomography scan[4]. A chemical fusion of mAb MOC31 with the exotoxin-A (ETA) led to growth delay for large tumors (120 mm$^3$) in nude mice, and it was proposed that the reduction of the targeting antibody in size would increase the efficiency[8]. It remains to be tested whether the improved tissue penetration and faster clearance rate of the much smaller anti-EGP2 scFv fragment will yield better results or whether its increased ability to access to normal EGP-2-expressing epithelial tissues, not accessible to mAbs due to their molecular weight of 150 kDa[1], will limit the resolving power of the method. The improved scFv can serve as a building block for other recombinant molecule formats such as dimerized and multimerized scFv, Fab or (Fab)$^2$ [11] to optimize size- and avidity effects. They can also be fused to other effector domains in the construction of antibody fragment based therapeutics. A scFv MOC31-ETA fusion was in vitro on SW2 cells ten thousand times more toxic than the mab MOC31-fusion with ETA (Zimmermann, unpublished results). The original unmodified scFv MOC31 was also used for the construction of a diabody with CD3 specificity for T-cell retargeting. In this format scFv MOC31 appeared to be somehow stabilized and a half life of 12 h has been reported, but the yield was as poor as for scFv MOC31 alone[37] and an in vivo application was not reported so far.

During the modelling we noticed that the $V_H$ domain of the framework template 4D5 belongs to a different structural subclass than the loop donor MOC31. Since there are several examples in the literature in which a simple loop graft failed and the chimeras had to be rescued by multiple additional back-mutations[36], we directly designed a second chimera in which the structural subclass and core packing of MOC31 was retained. This involved changing of eight additional residues, mostly in the core, to the murine sequence, than essentially corresponding to a resurfacing of the MOC31 $V_H$ domain. These additional mutations had no effect on antigen affinity, but they had a beneficial effect on the stability of the chimera. The additional mutations in 4D5MOC-B yielded a molecule which behaved very similar to the very well behaved 4D5 scFv. This is remarkably, as 4D5MOC-B is further removed in sequence from 4D5 than 4D5MOC-A and suggests that it may be critical to maintain a framework class, as defined by residues H6, H7 and H9 throughout and not mix the framework as these residues are interrelated. Furthermore, while 4D5MOC-B is closer in sequence to MOC31, the latter molecule is the least stable of all.

Figure 1B:
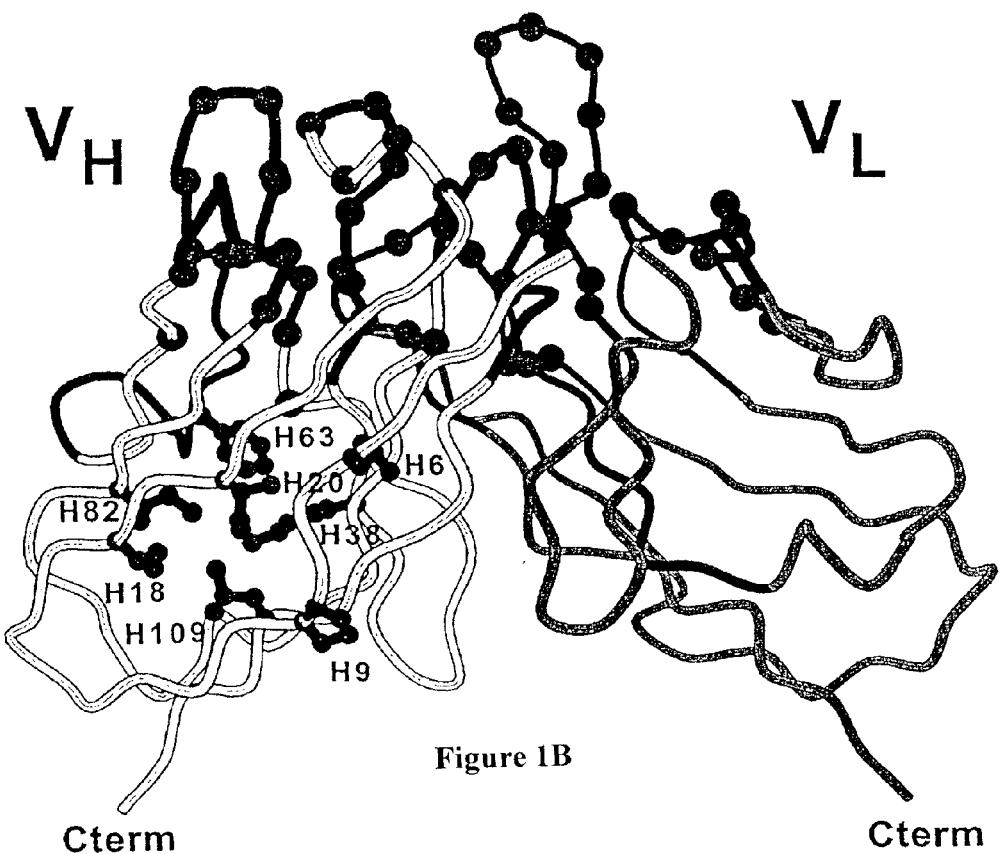
Figures 1C, 1D:
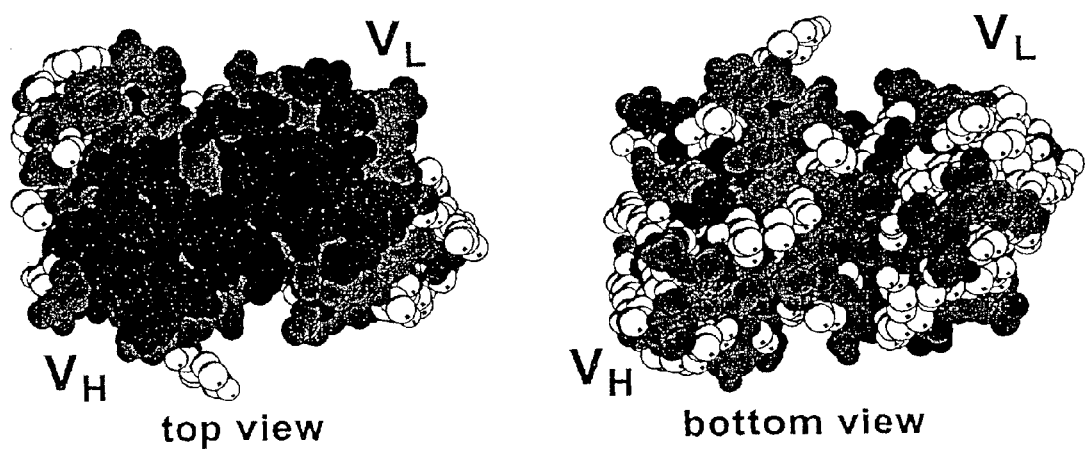

It has recently been shown that the $V_L$ domain of 4D5 is exceptionally stable and the thermodynamic stability of the 4D5 scFv is limited by intrinsic stability of its $V_H$ domain[20]. Grafting of the MOC31 antigen interaction surface onto this fragment resulted in a chimera of intermediate stability. This could be due to unfavorable interactions within the grafted loops or between grafted core residues and incompatible framework core residues. However, there are few contacts between those framework residues in the lower core which differ between 4D5 and MOC31 and core residues from the grafted loops, the two being separated by a layer of conserved residues (FIG. 1). The main direct contact between the residues changed in the loop graft and the group of residues additionally changed in 4D5MOC-B is between Met H48 (Val in 4D5) and Phe H63 (Val in 4D5 and in 4D5MOC-A). If there had been a steric clash in the original graft, we would have expected the situation to be aggravated by the substitution of the contact residue with a larger residue. It is therefore more likely that the destabilizing influence of the loops has been compensated by a general stabilization of the domain core.

The additional stabilization achieved by the core mutations in 4D5MOC-B was of crucial importance for effective enrichment at the tumor site. The most stable construct, 4D5MOC-B, enriched to 1.47% ID/g tissue with a tumor-to-blood ratio of 5.25. The aggregation-prone MOC31 was cleared from the circulation much more slowly than the more stable control antibodies and chimeras. It remains to be seen to what extent a further increase in stability can further improve the total dose enrichment and tumor-to-blood ratios.

We demonstrate in this study that the strategy of engineering for folding and stability is general tool for the improvement of interesting antibody-fragments. We used as an example the conversion of an unstable and poorly expressing murine anti-EGP-2 scFv, which failed in vivo, to a well expressing and very stable humanized antibody fragment of the same specificity. E also report in vivo targeting of EGP-2 presenting xenografts in CD1 nude mice for the first time. The engineered scFv 4D5MOC-B overcomes the limitations of scFv MOC31 and will be an important a building block for the development of new imaging and therapeutic antibody fragment-based reagents, directed to EGP-2 expressing carcinomas. We believe that in addition to the use of large library repertoires from which new antibody fragments with outstanding properties can be selected, the engineering for folding and stability of recombinant molecules is of extraordinary importance for their widespread future use in all applications, and especially those in tumor medicine. It must be emphasized again that biophysical properties strongly influence the ability of a scFv fragment to target to a tumor site, even when the complementary determining regions and the binding constants are identical. This indicates that the biophysical properties of an antibody fragment have a far greater importance for the biological performance than has been generally appreciated up to now.

TABLE 1

Comparison of affinities and kinetic rate constants as determined by radioimmunoassay (RIA) on SW2 cells and surface Plasmon resonance (Biacore)

| Antibody | RIA on SW2 Cells | | Surface Plasmon resonance (SPR) | |
|---|---|---|---|---|
| | $Kd^*$ (nM) | $Kd^\Delta$ (nM) | $K_{on}$ ($10^5 M^{-1} s^{-1}$) | $K_{off}$ ($10^{-3} s^{-1}$) |
| scFv MOC31 | 10.8 ± 2.6 | 3.0 | 0.99 ± 0.01 | 0.3 ± 0.01 |
| 4D5MOC-A | 3.6 ± 0.5 | 3.5 | 1.29 ± 0.001 | 0.45 ± 0.001 |
| 4D5MOC-B | 3.7 ± 0.5 | 3.9 | 1.84 ± 0.02 | 0.717 ± 0.001 |

Measurements were preformed at 4° C.* and 20° C.$^\Delta$

TABLE 2

Biodistribution of 99MTc-labled scFvs: in Babl/C-nude mice xenografted with SW2-tumors

| | ScFv MOC31 | | | FHTC-E2 |
|---|---|---|---|---|
| Organs | 1 h (n = 3) % ID/g | 4 h (n = 3) % ID/g | 24 h (n = 3) % ID/g | 24 h (n = 3) % ID/g |
| Blood | 8.46 ± 0.87 | 5.55 ± 1.98 | 1.34 ± 0.15 | 0.5 ± 0.13 |
| Heart | 5.1 ± 0.34 | 5.32 ± 1.36 | 1.39 ± 0.25 | 0.47 ± 0.23 |
| Lung | 7.37 ± 0.95 | 7.14 ± 1.61 | 2.09 ± 0.5 | 0.58 ± 0.16 |
| Spleen | 14.86 ± 1.91 | 17.84 ± 2.77 | 7.6 ± 0.56 | 1.2 ± 0.09 |
| Kidney | 253.69 ± 10.64 | 263.28 ± 43.1 | 117.4 ± 12.2 | 224.09 ± 40.4 |
| Stomach | 4.71 ± 1.04 | 4.08 ± 1.04 | 1.28 ± 0.21 | 0.25 ± 0.14 |
| Intestine | 5.85 ± 0.34 | 5.4 ± 1.97 | 1.56 ± 0.07 | 0.34 ± 0.04 |
| Liver | 35.03 ± 0.86 | 44.8 ± 9.54 | 20.38 ± 3.44 | 4.44 ± 0.65 |
| Muscle | 1.64 ± 0.23 | 1.57 ± 0.36 | 0.75 ± 0.82 | 0.31 ± 0.15 |
| Bone | 5.97 ± 0.41 | 6.01 ± 1.71 | 2.04 ± 0.68 | 0.57 ± 0.3 |
| Tumor | 2.46 ± 0.88 | 3.97 ± 1.07 | 1.24 ± 0.74 | 0.4 ± 0.2 |
| Tumor-to-blood ratio | 0.29 | 0.71 | 0.92 | 1.35 |

Biodistribution of $^{99m}$Tc-labeled scFv MOC31 and FITC-E2 was studied in eight week old female Balb/C nude mice which bear 17 days old SW2-tumors after injection of the radiolabeled antibodies into the animals. The numbers represent % injected dose per gram tissue (% ID/g). The results are expressed as the mean.

TABLE 3

Biodistribution of 99mtechnetium-labeled scFvs: in CD1-nude mice xenografted with SW2-tumors

| | 4D5MOC-B | | | 4D5MOC-A | FITC-E2 |
|---|---|---|---|---|---|
| Organs | 1 h (n = 3) % ID/g | 4 h (n = 3) % ID/g | 24 h (n = 3) % ID/g | 24 h (n = 3) % ID/g | 24 h (n = 3) % ID/g |
| Blood | 2.92 ± 0.47 | 1.31 ± 0.23 | 0.28 ± 0.06 | 0.43 ± 0.20 | 0.17 ± 0.02 |
| Heart | 0.97 ± 0.21 | 0.57 ± 0.11 | 0.28 ± 0.09 | 0.63 ± 0.18 | 0.16 ± 0.04 |
| Lung | 3.2 ± 1.29 | 1.2 ± 0.08 | 1.14 ± 0.60 | 1.77 ± 0.95 | 0.24 ± 0.05 |
| Spleen | 0.61 ± 0.06 | 0.67 ± 0.19 | 0.7 ± 0.13 | 1.57 ± 0.44 | 0.22 ± 0.04 |
| Kidney | 120.79 ± 7.19 | 140.56 ± 3.94 | 300.17 ± 85.2 | 90.53 ± 52.4 | 383.91 ± 57.3 |

TABLE 3-continued

Biodistribution of 99mtechnetium-labeled scFvs: in CD1-nude mice xenografted with SW2-tumors

| | 4D5MOC-B | | | 4D5MOC-A | FITC-E2 |
|---|---|---|---|---|---|
| Organs | 1 h (n = 3) % ID/g | 4 h (n = 3) % ID/g | 24 h (n = 3) % ID/g | 24 h (n = 3) % ID/g | 24 h (n = 3) % ID/g |
| Stomach | 0.48 ± 0.09 | 0.49 ± 0.1 | 0.24 ± 0.21 | 0.26 ± 0.07 | 0.26 ± 0.13 |
| Intestine | 1.33 ± 0.64 | 0.71 ± 0.06 | 0.30 ± 0.07 | 0.48 ± 0.15 | 0.21 ± 0.07 |
| Liver | 6.49 ± 1.53 | 6.86 ± 0.32 | 2.38 ± 0.52 | 4.37 ± 1.87 | 1.33 ± 0.33 |
| Muscle | 0.27 ± 0.01 | 0.17 ± 0.03 | 0.1 ± 0.02 | 0.21 ± 0.09 | 0.07 ± 0.01 |
| Bone | 0.29 ± 0.21 | 0.21 ± 0.16 | 0.06 ± 0.05 | 0.25 ± 0.31 | 0.06 ± 0.05 |
| Tumor | 1.74 ± 0.51 | 1.82 ± 0.22 | 1.47 ± 0.32 | 0.84 ± 0.38 | 0.23 ± 0.04 |
| Tumor to blood ratio | 0.59 | 1.38 | 5.25 | 1.95 | 1.35 |

Biodistribution of $^{99m}$Tc-labeled scFv 4D5MOC-1, 4D5MOC-B and FITC-E2 was studied in eight week old female CD1 nude mice which bear 13 days old SW2-tumors after injection of the radiolabeled antibodies into the animals. The numbers represent % injected dose per gram tissue (% ID/g). The results are expressed as the mean.

LITERATURE

1. De Leij, L., Helrich, W., Stein, R. & Mattes, M. J. SCLC-cluster-2 antibodies detect the pancarcinoma/epithelial glycoprotein EGP-2. Int J Cancer Suppl 8, 60-3 (1994).
2. Riethmuller, G. et al. Randomised trial of monoclonal antibody for adjuvant therapy of resected Dukes' C colorectal carcinoma. German Cancer Aid 17-1A Study Group [see comments]. Lancet 343, 1177-83 (1994).
3. Elias, D. J. et al. Phase I clinical comparative study of monoclonal antibody KS1/4 and KS1/4-methotrexate immunconjugate in patients with non-small cell lung carcinoma. Cancer Res 50, 4154-9 (1990).
4. Kosterink, J. G. et al. Pharmacokinetics and scintigraphy of indium-111-DTPA-MOC-31 in small-cell lung carcinoma. J Nucl Med 36, 2356-62 (1995).
5. Litvinov, S. V., Velders, M. P., Bakker, H. A., Fleuren, G. J. & Warnaar, S. O. Ep-CAM: a human epithelial antigen is a homophilic cell-cell adhesion molecule. J Cell Biol 125, 437-46 (1994).
6. Cirulli, V. et al. KSA antigen Ep-CAM mediates cell-cell adhesion of pancreatic epithelial cells: morphoregulatory roles in pancreatic islet development. J Cell Biol 140, 1519-34 (1998).
7. Basak, S. et al. Colorectal carcinoma invasion inhibition by CO17-1A/GA733 antigen and its murine homologue [see comments]. J Natl Cancer Inst 90, 691-7 (1998).
8. Zimmermann, S. et al. A novel immunotoxin recognising the epithelial glycoprotein-2 has potent antitumoural activity on chemotherapy-resistant lung cancer. Cancer Immunol Immunother 44, 1-9 (1997).
9. Huston, J. S. et al. Medical applications of single-chain antibodies. Int Rev Immunol 10, 195-217 (1993).
10. Carter, P. & Merchant, A. M. Engineering antibodies for imaging and therapy. Curr Opin Biotechnol 8, 449-54 (1997).
11. Pluckthun, A. & Pack, P. New protein engineering approaches to multivalent and bispecific antibody fragments. Immunotechnology 3, 83-105 (1997).
12. Bird, R. E. et al. Single-chain antigen-binding proteins [published erratum appears in Science 1989 Apr. 28; 244 (4903):409]. Science 242, 423-6 (1988).
13. Huston, J. S. et al. Protein engineering of antibody binding sites: recovery of specific activity in an anti-digoxin single-chain Fv analogue produced in Escherichia coli. Proc Natl Acad Sci USA 85, 5879-83 (1988).
14. Skerra, A. & Pluckthun, A. Assembly of a functional immunoglobulin Fv fragment in Escherichia coli. Science 240, 1038-41 (1988).
15. Vaughan, T. J. et al. Human antibodies with sub-nanomolar affinities isolated from a large non-immunized phage display library [see comments]. Nat Biotechnol 14, 309-14 (1996).
16. Krebber, A. et al. Reliable cloning of functional antibody variable domains from hybridomas and spleen cell repertoires employing a reengineered phage display system. Journal of Immunological Methods 201, 35-55 (1997).
17. Verhaar, M. J. et al. A single chain Fv derived from a filamentous phage library has distinct tumor targeting advantages over one derived from a hybridoma. Int J Cancer 61, 497-501 (1995).
18. Jung, S. & Pluckthun, A. Improving in vivo folding and stability of a single-chain Fv antibody fragment by loop grafting. Protein Eng 10, 959-66 (1997).
19. Carter, P. et al. Humanization of an anti-p185HER2 antibody for human cancer therapy. Proc Natl Acad Sci USA 89, 4285-9 (1992).
20. Worn, A. & Pluckthun, A. An intrinsically stable antibody scFv fragment can tolerate the loss of both disulfide bonds and fold correctly. FEBS Lett 427, 357-61 (1998).
21. Knappik, A. & Pluckthun, A. Engineered turns of a recombinant antibody improve its in vivo folding. Protein Eng 8, 81-9 (1995).
22. Pokkuluri, P. R. et al. Preparation, characterization and crystallization of an antibody Fab fragment that recognizes RNA. Crystal structures of native Fab and three Fab-mononucleotide complexes. Journal of Molecular Biology 243, 283-97 (1994).
23. Tulip, W. R., Varghese, J. N., Webster, R. G., Layer, W. G. & Colman, P. M. Crystal structures of two mutant neuraminidase-antibody complexes with amino acid substitutions in the interface. Journal of Molecular Biology 227, 149-59 (1992).
24. Tulip, W. R., Varghese, J. N., Layer, W. G., Webster, R. G. & Colman, P. M. Refined crystal structure of the influenza virus N9 neuraminidase-NC41 Fab complex. Journal of Molecular Biology 227, 122-48 (1992).
25. Shoham, M. Crystal structure of an anticholera toxin peptide complex at 2.3 A. Journal of Molecular Biology 232, 1169-75 (1993).
26. Eigenbrot, C., Randal, M., Presta, L., Carter, P. & Kossiakoff, A. A. X-ray structures of the antigen-binding domains from three variants of humanized anti-p185HER2 antibody 4D5 and comparison with molecular modeling. Journal of Molecular Biology 229, 969-95 (1993).
27. Prodromou, C. & Pearl, L. H. Recursive PCR: a novel technique for total gene synthesis. Protein Eng 5, 827-9 (1992).
28. Tang, Y., Jiang, N., Parakh, C. & Hilvert, D. Selection of linkers for a catalytic single-chain antibody using phage display technology. J Biol Chem 271, 15682-6 (1996).
29. Lindmo, T., Boven, E., Cuttitta, F., Fedorko, J. & Bunn, P. A., Jr. Determination of the immunoreactive fraction of radiolabelled monoclonal antibodies by linear extrapolation to binding at infinite antigen excess. J Immunol Methods 72, 77-89 (1984).
30. Roovers, R. C. et al. High-affinity recombinant phage antibodies to the pan-carcinoma marker epithelial glycoprotein-2 for tumour targeting. Br J Cancer 78, 1407-16 (1998).
31. Saul, F. A. & Poljak, R. J. Structural patterns at residue positions 9, 18, 67 and 82 in the VH framework regions of human and murine immunoglobulins. J Mol Biol 230, 15-20 (1993).
32. Langedijk, A. C. et al. The nature of antibody heavy chain residue H6 strongly influences the stability of a VH domain lacking the disulfide bridge. J Mol Biol 283, 95-110 (1998).
33. Bothmann, H. & Pluckthun, A. Selection for a periplasmic factor improving phage display and functional periplasmic expression.
34. Adams, G. P. et al. Increased affinity leads to improved selective tumor delivery of single-chain Fv antibodies. Cancer Res 58, 485-90 (1998).
35. Proba, K., Worn, A., Honegger, A. & Pluckthun, A. Antibody scFv fragments without disulfide bonds made by molecular evolution. J Mol Biol 275, 245-53 (1998).
36. Baca, M., Presta, L. G., O'Connor, S. J. & Wells, J. A. Antibody humanization using monovalent phage display. J Biol Chem 272, 10678-84 (1997).
37. Helfrich, W. et al. Construction and characterization of a bispecific diabody for retargeting T cells to human carcinomas. Int J Cancer 76, 232-9 (1998).
Allazikani, B., Lesk, A. M. & Chothia, C. (1997). STANDARD CONFORMATIONS FOR THE CANONICAL STRUCTURES OF IMMUNOGLOBULINS. J. Mol. Biol. 273, 927-948.
Alberto, R., Schibli, R., Egli, A., Schubiger, P. A., Abram, U. & Kaden T. A. (1998). A novel organometallic aqua complex of technetium for labeling of biomolecules: Synthesis of [99mTc(OH2)3(CO3)]+from [99mTcO4]− in aqueous solution and 1st reaction with a bifunctional ligand. J. Am. Chem. Soc. 120, 7987-7988.
Better, M., Chang, P., Robinson, R. & Horwitz, A. H. (1988). E. coli secretion of an active chimeric antibody fragment. Science 240, 1041-1043.
Blake, M. S., Johnston, K. H., Russel-Jones, G. J. & Gotschlich, E. C. (1984). A rapid, sensitive method for detection of alkaline phosphatase-conjugated anti-antibody on Western blots. Anal. Biochem. 136, 175-179.
Brinkmann, U., Reiter, Y., Jung, S., Lee, B. & Pastan, I. (1993). A recombinant immunotoxin containing a disulfide-stabilized Fv fragment. Proc. Natl. Acad. Sci. U.S.A. 90, 7538-7542.
COLMAN, P. M., LAVER, W. G., VARGHESE, J. N., BAKER, A. T., TULLOCH, P. A., AIR, G. M. & WEBSTER, R. G. (1987). THREE-DIMENSIONAL STRUCTURE OF A COMPLEX OF ANTIBODY WITH INFLUENZA VIRUS NEURAMINIDASE, NATURE 326, 358.

Glockshuber, R., Malia, M., Pfitzinger, I. & Plückthun, A. (1992). A comparison of strategies to stabilize immunoglobulin Fv-fragments. Biochemistry 29, 1362-1366.
Hiatt, A. (1990). Antibodies produced in plants. Nature 344, 469-470.
Hiatt, A. & Ma, J. K. (1993). Characterization and applications of antibodies produced in plants. Int. Rev. Immunol. 10, 139-152.
Hochuli, E., Bannwarth, W., Döbeli, H., Gentz, R. & Stüber, D. (1988). Genetic approach to facilitate purification of recombinant proteins with a novel metal chelate adsorbent. Bio/Technology 6, 1321-1325.
Hopp, T. P., Prickett, K. S., Price, V. L., Libby, R. T., March, C. J., Cerretti, D. P., Urdal, D. L. & Conlon, P. J. (1988). A short polypeptide marker sequence useful for recombinant protein identification and purification. Bio/Technology 6, 1204-1210.
Horwitz, A. H., Chang, C. P., Better, M., Hellstrom, K. E. & Robinson, R. R. (1988). Secretion of functional antibody and Fab fragment from yeast cells. Proc. Natl. Acad. Sci. U.S.A. 85, 8678-8682.
Kabat, E. A., Wu, T. T., & Bilofsky, H. (1979). Sequences of Immunoglobulin Chains, National Institutes of Health. NIH Publication 80-2008.
Kabat, E. A., Wu, T. T., Perry, H. M., Gottesmann, K. S. & Foeller, C. (1991). Sequences of proteins of immunological interest. U.S. Dept. of Health and Human Services, Public Health Service, National Institutes of Health. NIH Publication 91-3242.
Knappik, A. & Plückthun, A. (1994). An improved affinity tag based on the FLAG peptide for detection and purification of recombinant antibody fragments. BioTechniques 17, 754-761.
Knappik, A. & Plückthun, A. (1995). Engineered turns of a recombinant antibody improve its in vivo folding. Protein Eng. 8, 81-89.
Lindner, P., Guth, B., Wülfing, C., Krebber, C., Steipe, B., Müller, F. & Plückthun, A. (1992). Purification of native proteins from the cytoplasm and periplasm of Escherichia coli using IMAC and histidine tails: a comparison of proteins and protocols. Methods: A Companion to Methods Enzymol. 4, 41-56.
Nyyssönen, E., Penttila, M., Harkki, A., Saloheimo, A., Knowles, J. K. & Keranen, S. (1993). Efficient production of antibody fragments by the filamentous fungus Trichoderma reesei. Bio/Technology 11, 591-595.
Pack, P. & Plückthun, A. (1992). Miniantibodies: use of amphipathic helices to produce functional, flexibly linked dimeric Fv fragments with high avidity in Escherichia coli. Biochemistry 31, 1579-1584.
Pack, P., Kujau, M., Schroeckh, V., Knüpfer, U., Wenderoth, R., Riesenberg D. & Plückthun, A. (1993). Improved bivalent miniantibodies, with identical avidity as whole antibodies, produced by high cell density fermentation of in Escherichia coli. Bio/Technology 11, 1271-1277.
Pack, P. (1994). Mini-Antikörper: Bivalente, tetravalente und bispezifische Immunglobuline aus E. coli. Ph.D. thesis, Ludwig-Maximilians-Universität München.
Potter, K. N., Li, Y. & Capra, J. D. (1993). Antibody production in the baculovirus expression system. Int. Rev. Immunol. 10, 103-112.
Ridder, R., Schmitz, R., Legay, F. & Gram, H. (1995). Generation of rabbit monoclonal antibody fragments from a combinatorial phage display library and their production in the yeast Pichia pastoris. Bio/Technology 13, 255-260.

Rosenberg, S. A. & Lotze, M. T. (1986). Cancer immunotherapy using interleukin-2 and interleukin-2 activated lymphocytes. Ann. Rev. Immunol. 4, 681-709.

SHOHAM, M., PROCTOR, P., HUGHES, D. & BALDWIN, E. T. (1991). CRYSTAL PARAMETERS AND MOLECULAR REPLACEMENT OF AN ANTICHOLERA TOXIN PEPTIDE COMPLEX, PROTEINS. STRUCT. FUNCT. 11, 218.

Skerra, A. & Plückthun (1988). Assembly of a functional immunoglobulin Fv fragment in *Escherichia coli*. Science 240, 1038-1041.

Trill, J. J., Shatzman, A. R. & Ganguly, S. (1995). Production of monoclonal antibodies in COS and CHO cells. Curr. Opin. Biotechnol. 6, 553-560.

TULIP, W. R., VARGHESE, J. N., WEBSTER, R. G., AIR, G. M., LAVER, W. G. & COLMAN, P. M. (1989). CRYSTAL STRUCTURES OF NEURAMINIDASE-ANTIBODY COMPLEXES, COLD SPRING HARBOR SYMP. QUANT. BIOL. 54, Pt. 1, 257-63.

Ullrich, H. D., Patten, P. A., Yang, P. L., Romesberg, F. E. & Schultz, P. G. (1995). Expression studies of catalytic antibodies. Proc. Natl. Acad. Sci. USA 92, 11907-11911.

Vitetta, E. S., Thorpe, P. E. & Uhr, J. (1993). Immunotoxins: magic bullets or misguided missiles. Immunol. Today 14, 253-259.

Waibel, R., Alberto, R., Willuda, J., Finnern, R., Schibli, R., Stichelberger, A., Egli, A., Abram, U., Mach, J. P., Pluckthun, A. & Schubiger, P. A. (1999) Nature Biotechnol. 17, 897-901.

Ward, V. K., Kreissig, S. B., Hammock, B. D. & Choudary, P. V. (1995). Generation of an expression library in the baculovirus expression vector system. J. Virol. Methods 53, 263-272.

Whitelam, G. C., Cockburn, W. & Owen, M. R. (1994). Antibody production in transgenic plants. Biochem. Soc. Trans. 22, 940-944.

Willuda, J., Honegger, A., Waibel, R., Schubiger, P. A., Stahel, R., Zangemeister-Wittke, U. & Pluckthun, A. (1999) Cancer Res. 59, 5758-5767.

Wu, X. C., Ng, S. C., Near, R. I. & Wong, S. L. (1993). Efficient production of a functional single-chain anti-digoxin antibody via an engineered *Bacillus subtilis* expression-secretion system. Bio/Technology 11, 71-76.

NACCESS

S. Hubbard and J. Thornton, 1992, http://_sjh.bi.umist.ac.uk/naccess.html

Algorithm: Lee & Richards (1971, J. Mol. Biol., 55, 379-400)

Vbase:http://_www.mrc-cpe.cam.ac.uk/imt-doc/

Ian Tomlinson, imt@mrc-lmb.cam.ac.uk, fax +44 1223 402140

MRC Centre for Protein Engineering, Hills Road, Cambridge CB2 2QH, U.K.

IMGT: http://_www.ebi.ac.uk/imgt/

This display may be copied and redistributed freely, without advance permission, provided that it is referred to IMGT, and cited as: "IMGT, the international ImMunoGeneTics database http://_imgt.cnusc.fr:8104 (Coordinator: Marie-Paule Lefranc, Montpellier, France lefranc@limgm.igh.cnrs.fr). For reference: Nucleic Acids Research, 25, 206-211 (1997)."

SEQUENCE LISTING

```
SEQ-ID No. 1:
human anti-c-ErbB2 scFv fragment 4D5:
DIQMTQSPSSLSASVGDRVTITCRASQDVNTAVAWYQQKPGKAPKLLIYS
ASFLYSGVPSRFSGSRSGTDFTLTISSLQPEDFATYYCQQHYTTPPTFGQ
GTKVEIKRTPSHNSHQVPSAGGPTANSGTSGSEVQLVESGGGLVQPGGSL
RLSCAASGFNIKDTYIHWVRQAPGKGLEWVARIYPTNGYTRYADSVKGRF
TISADTSKNTAYLQMNSLRAEDTAVYYCSRWGGDGFYAMDYWGQGTLVTV
SS SEQ-ID No. 2:
anti-EGP-2 scFv fragment obtained from the murine
hybridoma MOC31
DIVMTQSAFSNPVTLGTSASISCRSTKSLLHSNGITYLYWYLQKPGQSPQ
LLIYQMSNLASGVPDRFSSSGSGTDFTLRISRVEAEDVGVYYCAQNLEIP
RTFGGGTKLEIKRTPSHNSHQVPSAGGPTANSGTSGSQVQLQQSGPELKK
PGETVKISCKASGYTFTNYGMNWVKQAPGRGLKWMGWINTYTGESTYADD
FKGRFAFSLETSASAAYLQINNLKNEDTATYFCARFAIKGDYWGQGTTLT
VSS SEQ-ID No. 3:
anti-EGP-2 scFv fragment 4D5MOC-B
DIQMTQSPSSLSASVGDRVTITCRSTKSLLHSNGITYLYWYQQKPGKAPK
LLIYQMSNLASGVPSRFSSSGSGTDFTLTISSLQPEDFATYYCAQNLEIP
RTFGQGTKVELKRTPSHNSHQVPSAGGPTANSGTSGSEVQLVQSGPGLVQ
PGGSVRISCAASGYTFTNYGMNWVKQAPGKGLEWMGWINTYTGESTYADS
FKGRFTFSLDTSASAAYLQINSLRAEDTAVYYCARFAIKGDYWGQGTLLT
VSS
```

The invention claimed is:

1. A composition comprising an antigen-binding immunoglobulin or immunoglobulin fragment thereof that comprises
   i) VH domain antigen-binding loops from a donor immunoglobulin or immunoglobulin fragment (donor) which is able to bind to an antigen, and
   ii) VH domain framework regions from an acceptor immunoglobulin or immunoglobulin fragment (acceptor), wherein the VH domains of said donor and of said acceptor belong to different framework structure subgroups, and wherein in the chimera one or more of the residues present at identified framework positions in the acceptor are replaced by those present at corresponding positions in the donor so that the chimera has increased stability as compared to a chimera wherein the identified framework positions are not replaced, wherein said identified framework positions are selected from the group consisting of H6, H7, H8, H9, H10, H18, H20, H38, H63, H67, H82 and H109 in said VH domains, and wherein said chimera is able to bind to said antigen, said immunoglobulin or fragment thereof being attached to a moiety selected from the group consisting of a detection tag, a purification tag, a reporter molecule or an effector molecule.

2. A composition according to claim 1 wherein the antigen-binding immunoglobulin or immunoglobulin fragment is attached to an effector molecule.

3. A composition according to claim 2 wherein the effector molecule is therapeutic.

4. A composition according to claim 3 wherein the effector molecule is a toxin molecule.

5. A composition according to claim 4 wherein the toxin is *Pseudomonas* exotoxin A or a fragment or variant thereof.

6. A composition according to claim 4 wherein the antigen-binding immunoglobulin fragment is the anti-EGP-2 scFv fragment 4D5MOC-B (SEQ. ID. No. 3).

7. A composition according to claim 5 wherein the antigen-binding immunoglobulin fragment is the anti-EGP-2 scFv fragment 4D5MOC-B (SEQ. ID. No. 3).

* * * * *

UNITED STATES PATENT AND TRADEMARK OFFICE
CERTIFICATE OF CORRECTION

PATENT NO.         : 7,858,088 B2                                    Page 1 of 1
APPLICATION NO.    : 11/969059
DATED              : December 28, 2010
INVENTOR(S)        : Andreas Plückthun et al.

It is certified that error appears in the above-identified patent and that said Letters Patent is hereby corrected as shown below:

Column 36, line 56
        Please delete "4DSMOC-B" and insert therefor --4D5MOC-B--.

Signed and Sealed this
First Day of March, 2011

David J. Kappos
*Director of the United States Patent and Trademark Office*

SEQUENCE LISTING

```
<160> NUMBER OF SEQ ID NOS: 12

<210> SEQ ID NO 1
<211> LENGTH: 252
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Pro Ser His
            100                 105                 110

Asn Ser His Gln Val Pro Ser Ala Gly Gly Pro Thr Ala Asn Ser Gly
        115                 120                 125

Thr Ser Gly Ser Glu Val Gln Leu Val Glu Ser Gly Gly Gly Leu Val
130                 135                 140

Gln Pro Gly Gly Ser Leu Arg Leu Ser Cys Ala Ala Ser Gly Phe Asn
145                 150                 155                 160

Ile Lys Asp Thr Tyr Ile His Trp Val Arg Gln Ala Pro Gly Lys Gly
                165                 170                 175

Leu Glu Trp Val Ala Arg Ile Tyr Pro Thr Asn Gly Tyr Thr Arg Tyr
            180                 185                 190

Ala Asp Ser Val Lys Gly Arg Phe Thr Ile Ser Ala Asp Thr Ser Lys
        195                 200                 205

Asn Thr Ala Tyr Leu Gln Met Asn Ser Leu Arg Ala Glu Asp Thr Ala
210                 215                 220

Val Tyr Tyr Cys Ser Arg Trp Gly Gly Asp Gly Phe Tyr Ala Met Asp
225                 230                 235                 240

Tyr Trp Gly Gln Gly Thr Leu Val Thr Val Ser Ser
                245                 250

<210> SEQ ID NO 2
<211> LENGTH: 253
<212> TYPE: PRT
<213> ORGANISM: Mus sp.

<400> SEQUENCE: 2

Asp Ile Val Met Thr Gln Ser Ala Phe Ser Asn Pro Val Thr Leu Gly
  1               5                  10                  15

Thr Ser Ala Ser Ile Ser Cys Arg Ser Thr Lys Ser Leu Leu His Ser
             20                  25                  30

Asn Gly Ile Thr Tyr Leu Tyr Trp Tyr Leu Gln Lys Pro Gly Gln Ser
         35                  40                  45

Pro Gln Leu Leu Ile Tyr Gln Met Ser Asn Leu Ala Ser Gly Val Pro
 50                  55                  60

Asp Arg Phe Ser Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
                 85                  90                  95

Leu Glu Ile Pro Arg Thr Phe Gly Gly Gly Thr Lys Leu Glu Ile Lys
            100                 105                 110

Arg Thr Pro Ser His Asn Ser His Gln Val Pro Ser Ala Gly Gly Pro
        115                 120                 125

Thr Ala Asn Ser Gly Thr Ser Gly Ser Gln Val Gln Leu Gln Gln Ser
130                 135                 140

Gly Pro Glu Leu Lys Lys Pro Gly Glu Thr Val Lys Ile Ser Cys Lys
145                 150                 155                 160

Ala Ser Gly Tyr Thr Phe Thr Asn Tyr Gly Met Asn Trp Val Lys Gln
                165                 170                 175

Ala Pro Gly Arg Gly Leu Lys Trp Met Gly Trp Ile Asn Thr Tyr Thr
```

-continued

```
                180             185             190
Gly Glu Ser Thr Tyr Ala Asp Asp Phe Lys Gly Arg Phe Ala Phe Ser
            195                 200                 205

Leu Glu Thr Ser Ala Ser Ala Ala Tyr Leu Gln Ile Asn Asn Leu Lys
        210                 215                 220

Asn Glu Asp Thr Ala Thr Tyr Phe Cys Ala Arg Phe Ala Ile Lys Gly
225                 230                 235                 240

Asp Tyr Trp Gly Gln Gly Thr Thr Leu Thr Val Ser Ser
            245                 250
```

<210> SEQ ID NO 3
<211> LENGTH: 253
<212> TYPE: PRT
<213> ORGANISM: Artificial Sequence
<220> FEATURE:
<223> OTHER INFORMATION: Description of Artificial Sequence: anti-EGP-2
      scFv fragment 4D5MOC-B

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg Thr Pro Ser His Asn Ser His Gln Val Pro Ser Ala Gly Gly Pro
        115                 120                 125

Thr Ala Asn Ser Gly Thr Ser Gly Ser Glu Val Gln Leu Val Gln Ser
130                 135                 140

Gly Pro Gly Leu Val Gln Pro Gly Gly Ser Val Arg Ile Ser Cys Ala
145                 150                 155                 160

Ala Ser Gly Tyr Thr Phe Thr Asn Tyr Gly Met Asn Trp Val Lys Gln
                165                 170                 175

Ala Pro Gly Lys Gly Leu Glu Trp Met Gly Trp Ile Asn Thr Tyr Thr
            180                 185                 190

Gly Glu Ser Thr Tyr Ala Asp Ser Phe Lys Gly Arg Phe Thr Phe Ser
        195                 200                 205

Leu Asp Thr Ser Ala Ser Ala Ala Tyr Leu Gln Ile Asn Ser Leu Arg
    210                 215                 220

Ala Glu Asp Thr Ala Val Tyr Tyr Cys Ala Arg Phe Ala Ile Lys Gly
225                 230                 235                 240

Asp Tyr Trp Gly Gln Gly Thr Leu Leu Thr Val Ser Ser
            245                 250
```

<210> SEQ ID NO 4
<211> LENGTH: 113
<212> TYPE: PRT
<213> ORGANISM: Mus sp.

```
<400> SEQUENCE: 4

Asp Ile Val Met Thr Gln Ser Ala Phe Ser Asn Pro Val Thr Leu Gly
 1               5                  10                  15

Thr Ser Ala Ser Ile Ser Cys Arg Ser Thr Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Ile Pro Arg Thr Phe Gly Gly Gly Thr Lys Leu Glu Ile Lys
            100                 105                 110

Arg

<210> SEQ ID NO 5
<211> LENGTH: 113
<212> TYPE: PRT
<213> ORGANISM: Artificial Sequence
<220> FEATURE:
<223> OTHER INFORMATION: Description of Artificial Sequence: 4D5MOC-A
      peptide

<400> SEQUENCE: 5

Asp Ile Gln Met Thr Gln Ser Pro Ser Ser Leu Ser Ala Ser Val Gly
 1               5                  10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg

<210> SEQ ID NO 6
<211> LENGTH: 113
<212> TYPE: PRT
<213> ORGANISM: Artificial Sequence
<220> FEATURE:
<223> OTHER INFORMATION: Description of Artificial Sequence: Synthetic
      4D5MOC-B peptide

<400> SEQUENCE: 6

Asp Ile Gln Met Thr Gln Ser Pro Ser Ser Leu Ser Ala Ser Val Gly
 1               5                  10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45
```

```
Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg

<210> SEQ ID NO 7
<211> LENGTH: 108
<212> TYPE: PRT
<213> ORGANISM: Artificial Sequence
<220> FEATURE:
<223> OTHER INFORMATION: Description of Artificial Sequence: Synthetic
      4D5 peptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
            100                 105

<210> SEQ ID NO 8
<211> LENGTH: 116
<212> TYPE: PRT
<213> ORGANISM: Mus sp.

<400> SEQUENCE: 8

Gln Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Arg Gly Leu Lys Trp Met
        35                  40                  45

Gly Trp Ile Asn Thr Tyr Thr Gly Glu Ser Thr Tyr Ala Asp Asp Phe
    50                  55                  60

Lys Gly Arg Phe Ala Phe Ser Leu Glu Thr Ser Ala Ser Ala Ala Tyr
65                  70                  75                  80

Leu Gln Ile Asn Asn Leu Lys Asn Glu Asp Thr Ala Thr Tyr Phe Cys
                85                  90                  95

Ala Arg Phe Ala Ile Lys Gly Asp Tyr Trp Gly Gln Gly Thr Thr Leu
            100                 105                 110

Thr Val Ser Ser
            115
```

```
<210> SEQ ID NO 9
<211> LENGTH: 116
<212> TYPE: PRT
<213> ORGANISM: Artificial Sequence
<220> FEATURE:
<223> OTHER INFORMATION: Description of Artificial Sequence: Synthetic
      4D5MOC-A peptide

<400> SEQUENCE: 9

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Val
    50                  55                  60

Lys Gly Arg Phe Thr Phe Ser Leu Asp Thr Ser Ala Ser Ala Ala Tyr
65                  70                  75                  80

Leu Gln Met Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence: Synthetic
      4D5MOC-B peptide

<400> SEQUENCE: 10

Glu Val Gln Leu Val Gln Ser Gly Pro Gly Leu Val Gln Pro Gly Gly
 1               5                  10                  15

Ser Val Arg Ile Ser Cys Ala Ala Ser Gly Tyr Thr Phe Thr Asn Tyr
            20                  25                  30

Gly Met Asn Trp Val Lys Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Thr Phe Ser Leu Asp Thr Ser Ala Ser Ala Ala Tyr
65                  70                  75                  80

Leu Gln Ile Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Leu
            100                 105                 110

Thr Val Ser Ser
        115

<210> SEQ ID NO 11
<211> LENGTH: 120
<212> TYPE: PRT
<213> ORGANISM: Artificial Sequence
<220> FEATURE:
<223> OTHER INFORMATION: Description of Artificial Sequence: Synthetic
      4D5 peptide

<400> SEQUENCE: 11
```

-continued

```
Glu Val Gln Leu Val Glu Ser Gly Gly Leu Val Gln Pro Gly Gly
 1               5                  10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence:  Linker
      peptide

<400> SEQUENCE: 12

Thr Pro Ser His Asn Ser His Gln Val Pro Ser Ala Gly Gly Pro Thr
 1               5                  10                  15

Ala Asn Ser Gly Thr Ser Gly Ser
                20
```